United States Patent
Sela et al.

(10) Patent No.: US 10,463,447 B2
(45) Date of Patent: Nov. 5, 2019

(54) SYSTEM AND METHOD FOR DETECTING AND ADJUSTING REFERENCE MARKER ERRORS IN SURGICAL NAVIGATION SYSTEMS

(71) Applicants: Gal Sela, Toronto (CA); Arun Victor Jagga, Mississauga (CA)

(72) Inventors: Gal Sela, Toronto (CA); Arun Victor Jagga, Mississauga (CA)

(73) Assignee: SYNAPTIVE MEDICAL (BARBADOS) INC., Bridgetown (BB)

(*) Notice: Subject to any disclaimer, the term of this patent is extended or adjusted under 35 U.S.C. 154(b) by 123 days.

(21) Appl. No.: 15/125,245

(22) PCT Filed: Sep. 15, 2014

(86) PCT No.: PCT/CA2014/050878
§ 371 (c)(1),
(2) Date: Sep. 12, 2016

(87) PCT Pub. No.: WO2015/135059
PCT Pub. Date: Sep. 17, 2015

(65) Prior Publication Data
US 2017/0069073 A1 Mar. 9, 2017

Related U.S. Application Data

(63) Continuation-in-part of application No. PCT/CA2014/050266, filed on Mar. 14, 2014.
(Continued)

(51) Int. Cl.
*A61B 34/20* (2016.01)
*A61B 90/00* (2016.01)
(Continued)

(52) U.S. Cl.
CPC ............... *A61B 90/39* (2016.02); *A61B 34/10* (2016.02); *A61B 34/20* (2016.02); *G06T 7/248* (2017.01);
(Continued)

(58) Field of Classification Search
CPC . A61B 34/20; A61B 34/30; A61B 2034/2055; A61B 2090/3983;
(Continued)

(56) References Cited

U.S. PATENT DOCUMENTS 6,279,579 B1* 8/2001 Riaziat ............... A61N 5/1049
128/897
9,706,868 B2* 7/2017 Karasz ............... A61B 90/50
(Continued)

FOREIGN PATENT DOCUMENTS

EP 2431003 A1 3/2012
WO 2013189520 A1 12/2013

OTHER PUBLICATIONS

Eckert et al., Age-related changes in processing speed: unique contributions of cerebellar and prefrontal cortex, Mar. 8, 2010 [retrieved Oct. 25, 2015], Frontiers in Human Neuroscience, vol. 4, Article 10,pp. 1-14. Retrieved: https://www.frontiersin.org/articles/10.3389/neuro.09.010.2010/full (Year: 2010).*
(Continued)

*Primary Examiner* — Andrew M Moyer
*Assistant Examiner* — Dennis Rosario
(74) *Attorney, Agent, or Firm* — Hill & Schumacher

(57) ABSTRACT

Systems, and methods are provided for computer based method for determining a source of a registration error in a surgical navigation system, by registering at least two patient reference markers in a common coordinate space, positioning at least one reference marker in a known position with respect to at least one of two patient reference
(Continued)

markers. A relative position of the at least two patient reference markers with respect to each other in the common coordinate space is monitored, as well as a position of said at least one reference marker with respect to a first of the at least two patient reference markers. Upon detecting a change in relative position of the least at least two patient reference markers with respect to each other, determining if the position of said at least one reference marker with respect to the first of the at least two patient reference markers has changed, and if yes, designating that the first patient reference marker has moved, and if not, designating that the second of the at least two patient reference markers has moved.

18 Claims, 21 Drawing Sheets

Related U.S. Application Data

(60) Provisional application No. 61/799,735, filed on Mar. 15, 2013, provisional application No. 61/801,530, filed on Mar. 15, 2013, provisional application No. 61/800,155, filed on Mar. 15, 2013, provisional application No. 61/818,280, filed on May 1, 2013, provisional application No. 61/924,993, filed on Jan. 8, 2014.

(51) Int. Cl.
*A61B 34/10* (2016.01)
*G06T 7/33* (2017.01)
*G06T 7/246* (2017.01)
*G06T 7/73* (2017.01)
*A61B 90/50* (2016.01)

(52) U.S. Cl.
CPC ............... *G06T 7/33* (2017.01); *G06T 7/337* (2017.01); *G06T 7/74* (2017.01); *A61B 90/50* (2016.02); *A61B 2034/104* (2016.02); *A61B 2034/107* (2016.02); *A61B 2034/2048* (2016.02); *A61B 2034/2051* (2016.02); *A61B 2034/2055* (2016.02); *A61B 2090/364* (2016.02); *A61B 2090/373* (2016.02); *A61B 2090/3929* (2016.02); *A61B 2090/3937* (2016.02); *A61B 2090/3983* (2016.02); *G06T 2207/10021* (2013.01); *G06T 2207/10048* (2013.01); *G06T 2207/10076* (2013.01); *G06T 2207/10081* (2013.01); *G06T 2207/10088* (2013.01); *G06T 2207/10104* (2013.01); *G06T 2207/10136* (2013.01); *G06T 2207/30016* (2013.01); *G06T 2207/30096* (2013.01); *G06T 2207/30101* (2013.01); *G06T 2207/30204* (2013.01)

(58) Field of Classification Search
CPC . A61B 2034/2051; A61B 46/00; A61B 90/10; A61B 90/39; A61B 1/00193; A61B 2046/205; A61B 2090/3937; A61B 2090/3954; A61B 34/10; A61B 2034/2048; A61B 2034/2068
See application file for complete search history.

(56) References Cited

U.S. PATENT DOCUMENTS

| | | |
|---|---|---|
| 2003/0056385 A1 | 3/2003 | Leitner et al. |
| 2012/0059220 A1 | 3/2012 | Holsing et al. |

OTHER PUBLICATIONS

Liao, Hognen, et al. "Real-time 3D-image-guided navigation system based on integral videography." International Symposium on Biomedical Optics. International Society for Optics and Photonics, 2002.
Written Opinion: PCT/CA2014/050878 dated Jan. 9, 2015.
International Search Report: PCT/CA2014/050878 dated Jan. 9, 2015.

* cited by examiner

| | | | |
|---|---|---|---|
| Patient Reference Marker (1100) | Null | Non-zero | Non-zero |
| Patient Reference Marker (1110) | Non-Zero | Null | Zero |
| Patient Reference Marker (1300) | Non-Zero | Zero | Null |

Figure 14

SYSTEM AND METHOD FOR DETECTING AND ADJUSTING REFERENCE MARKER ERRORS IN SURGICAL NAVIGATION SYSTEMS

CROSS-REFERENCE TO RELATED APPLICATIONS

This application claims priority to International Application No. CA/2014/050266, titled "SYSTEM AND METHOD FOR DYNAMIC VALIDATION, CORRECTION OF REGISTRATION FOR SURGICAL NAVIGATION" and filed on Mar. 14, 2014, the entire contents of which are incorporated herein by reference. The present system may be used with any compatible surgical navigation system. A non-limiting example of such a surgical navigation system is outlined in the PCT International application CA/2014/050270 entitled "SYSTEMS AND METHODS FOR NAVIGATION AND SIMULATION OF INVASIVE THERAPY", which claims the priority benefit of U.S. Provisional Patent Application Ser. No. 61/800,155 and 61/924,993, the entire contents of which are incorporated herein by reference.

FIELD

The present disclosure relates to an apparatus and method for minimizing accuracy errors in Surgical Navigation Systems employing a tracking system.

BACKGROUND

During a navigated surgical procedure a surgeon typically needs to correlate the position of previously acquired patient imaging (such as MRI), with the physical position of the patient who is to be operated on. This is typically achieved by employing a surgical navigation system that integrates both the patient imaging and the patients positioning into a common coordinate space. Navigated surgical procedures also generally employ surgical instruments that are also integrated within this common coordinate space. This common coordinate space is formed by an amalgamation of the virtual coordinate space of the system used to perform registration and the actual coordinate spaces. Wherein the actual coordinate space is defined as the space where actual objects such as the patient and tools exist and the tracking coordinate space will be defined as the space wherein only physical objects visible to the tracking detector are locatable such as tracking markers. Correlation of the patient imaging with the physical position of the patient is accomplished through the process of registration to this common coordinate space. Ensuring that the correlation is accurate is desirable and necessary for maintaining surgeon confidence in the information being presented to them and in ensuring the navigated procedure is optimally executed.

However, presently it tends to be difficult to maintain accurate correlation of patient imaging and positioning as described by the paper [The Silent Loss of Navigation Accuracy; Research-Human-Clinical Studies; Vol. 72, No. 5, May 2013, pages 796-807]. Presently this accuracy is typically reported to a surgeon as a confidence or tolerance number at the time that registration is computed. This number is not indicative of the complexity of registration accuracy, and, more significantly, is not indicative of the fact that accuracy can vary in different parts of the surgical field and throughout the progression of the procedure. Further, this number is used as a one-time accept/reject criterion for the registration—once the registration is accepted typically it is assumed to be correct for the duration of the procedure, or until the surgeon notices that something is significantly misaligned.

With the present state of the art inaccuracy of the navigation system is difficult to identify as a typical system only presents a virtual representation of the OR procedure, and as such it cannot be readily contrasted to the actual physical state of the OR at a given time. Currently, for a surgeon to measure registration accuracy during a procedure he or she typically locates the tool relative to an identifiable location on the actual patient anatomy while noting the degree to which the location of the virtual tool is displaced from the same location relative to the virtualized patient anatomy, where such a virtual tool is displayed as an overlay on the three-dimensional imaging data from a scan of the patient's anatomy. Furthermore, once a registration misalignment is noticed, correcting for the error tends to be difficult, and often not achievable. Thus the embodiments provided in this disclosure attempt to alleviate some of the aforementioned shortfalls of presently employed surgical navigation systems.

SUMMARY

The present disclosure discloses a computer based method for determining a source of a registration error in a surgical navigation system, comprising:
a) registering at least two patient reference markers in a common coordinate space;
b) positioning at least one reference marker in a known position with respect to at least one of said at least two patient reference markers;
c) monitoring
  a relative position of said at least two patient reference markers with respect to each other in said common coordinate space, and
  a position of said at least one reference marker with respect to a first of said at least two patient reference markers; and
d) upon detecting a change in relative position of said least at least two patient reference markers with respect to each other, determining if the position of said at least one reference marker with respect to the first of said at least two patient reference markers has changed, and if yes, designating that said first patient reference marker has moved, and if not, designating that a second of said at least two patient reference markers has moved.

The present disclosure provides a system for determining a source of a registration error in a surgical navigation system, comprising
a) two or more patient reference markers registered in a common coordinate space;
b) at least one reference marker in a known position with respect to at least one of said at least two patient reference markers;
c) one or more sensors configured to monitor
  a relative position of said at least two patient reference markers with respect to each other in said common coordinate space, and
  a position of said at least one reference marker with respect to a first of said at least two patient reference markers; and
d) a computer processor configured to receive an output from said one or more sensors, said computer processor being programmed with instructions to compute, based on said output from said one or more sensors, which of said two or more patient reference markers has moved.

In an embodiment there is provided a method for registering patient imaging to a patient during a surgical procedure comprising the steps of:
  registering the position of at least two patient reference markers in a common coordinate space
  registering a patients imaging with the patient in said common coordinate space containing the registered at least two patient reference markers,
  draping the patient and draping a first of the at least two patient reference markers and leaving a second of the at least two patient reference markers undraped,
  re-registering the first draped patient reference markers position to said common coordinate space,
  draping a second of the at least two patient reference markers, and
  re-registering the second of the at least two patient reference markers position to said common coordinate space.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 14 illustrates matrix for use in a flow chart.

DETAILED DESCRIPTION

Figure 1A:
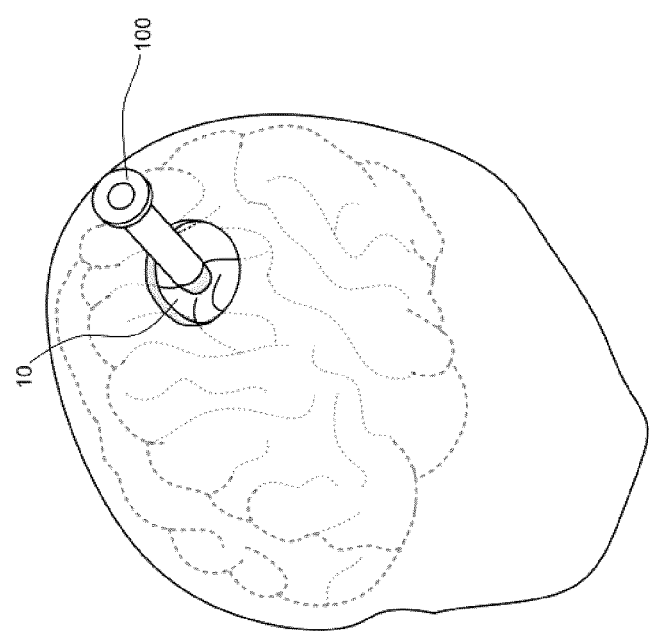
FIG. 1A illustrates the insertion of an access port into a human brain

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein the phrase "position" refers to any set of coordinates that may be used to define a point or object in any arbitrary coordinate space. The phrase "position" as defined herein may include coordinates for the position of a point or object with 6 degrees of freedom, those degrees of freedom may refer to the point or objects location in a physical space, for example x, y, and z coordinates as are commonly used to define such a location in physical space, those degrees of freedom also being able to define the objects pose, for example its pitch, yaw, and roll rotational coordinates as are commonly used to define such a pose. In addition the phrase "position" may be inclusive of more than just coordinates that refer to an objects location or pose but may also be used to define the state of that object such as its temperature. The phrase "position" shall not be limited by the examples provided here and may encompass any understanding of the term as it is known in the art.

As used herein the phrase "accurate" when referring to surgical navigation systems means registration of common reference coordinates (as defined below) in the common coordinate space is reflective of the actual position of the physical common reference coordinates position in the actual coordinate space.

Various apparatuses or processes will be described below to provide examples of embodiments of the invention. No embodiment described below limits any claimed invention and any claimed invention may cover processes or apparatuses that differ from those described below. The claimed inventions are not limited to apparatuses or processes having all of the features of any one apparatus or process described below or to features common to multiple or all of the apparatuses or processes described below. It is possible that an apparatus or process described below is not an embodiment of any claimed invention.

Furthermore, numerous specific details are set forth in order to provide a thorough understanding of the embodiments described herein. However, it will be understood by those of ordinary skill in the art that the embodiments described herein may be practiced without these specific details. In other instances, well known methods, procedures and components have not been described in detail so as not to obscure the embodiments described herein. Also, the description is not to be considered as limiting the scope of the embodiments described herein.

Furthermore, in the following passages, different aspects of the embodiments are defined in more detail. In particular, any feature indicated as being preferred or advantageous may be combined with at least one other feature or features indicated as being preferred or advantageous.

Embodiments of the present disclosure provide overlays of medical equipment for assisting a surgeon in visualizing a surgical area or object of interest such as a medical instrument, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

An example of an access port is an intracranial conduit which may be employed in neurological procedures in order to provide access to internal tissue pathologies, such as tumors. One example of an intracranial access port is the BrainPath™ surgical access port provided by NICO, which may be inserted into the brain via an obturator with an atraumatic tip. Such an access port may be employed during a surgical procedure, by inserting the access port, via the obturator that is received within the access port, through the white and gray of the brain to access a surgical site.

An example of a system used for registering objects to the common coordinate space is the Polaris system manufactured by NDI. Where a 3D tracking camera is able to detect the position of IR reflecting spheres such as provided by NDI And depicted as 200 in FIG. 2.

Minimally invasive brain surgery using access ports is a recently conceived method of performing surgery on brain tumors previously considered inoperable. One object of the present invention is to provide a system and method to assist in minimally invasive brain surgery. To address intracranial surgical concerns, specific products such as the NICO Brain-Path™ port have been developed for port-based surgery.

FIG. 1A illustrates the insertion of an access port 100 into a human brain 10, for providing access to internal brain tissue during a medical procedure. Surgical instruments (which includes any surgical equipment a surgeon may employ during a brain surgery including medical instruments such as scalpels, needles, biopsy probes, suctioning devices, scissors to mention just a few) may then be inserted within the lumen of the access port 100 in order to perform surgical, diagnostic and/or therapeutic procedures, such as resecting tumors as necessary.

As seen in FIG. 1A, port 100 is comprised of a cylindrical assembly formed of an outer sheath. Port 100 may accommodate an introducer (not shown) which is an internal cylinder that slidably engages the internal surface of port 100. The introducer may have a distal end in the form of a conical atraumatic tip to allow for insertion into the sulcal folds of the brain 10. Port 100 has a sufficient diameter to enable bimanual manipulation of the surgical instrument(s) within its annular volume such as suctioning devices, scissors, scalpels, and cutting devices as examples.

Figure 1B:
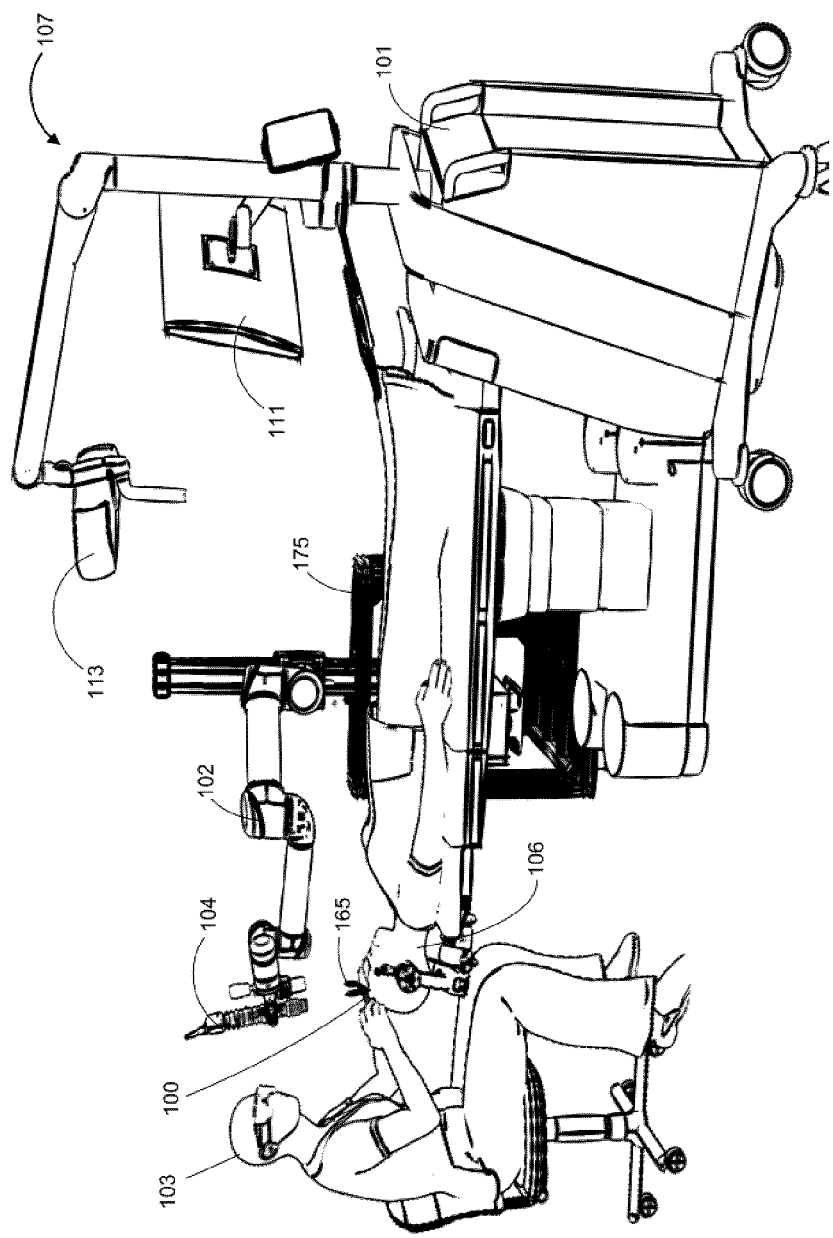
FIG. 1B illustrates a typical surgical navigation system.

FIG. 1B is a diagram illustrating components of an exemplary surgical system used in port based surgery. FIG. 1B shows a navigation system 107 having an equipment tower 101, tracking system 113, display 111 (for a graphical user interface), an intelligent positioning system 175 and tracking markers 165 used to track surgical instruments or access port 100. Tracking detector 113 may also be considered an optical tracking device which tracks the tracking markers 165. The tracking system may include a tracking camera. It should be noted that all tracking systems may be employed to register objects into a coordinate space, such as the common coordinate space described above. Generally all systems which are used to register objects to a coordinate space contain in some a tracking system of some type, which is any system that may be used to acquire the position of a landmark (or equivalently an object) in an arbitrary coordinate space (such as the common coordinate space described above).

As shown in FIG. 1B, surgeon 103 is resecting a tumor in the brain of a patient 106, through port 100. External scope 104, attached to automated arm 102, is typically used by the surgeon to enhance visibility of the brain at the distal end of the port 100. The external scope 104 may be zoomed-in or zoomed-out, and its output depicted on a visual display 111.

Tracking of Tools

Figure 2:
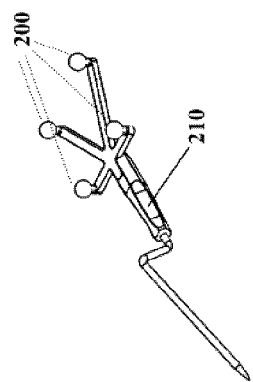
FIG. 2 illustrates a typical surgical navigation system pointer tool with attached locatable optical assembly.

FIG. 2 depicts an example surgical instrument 210 that is locatable in a coordinate space through detection of a tracking system component of a surgical navigation system. The locatable physical objects in said coordinate space are shown as tracking markers 200 in this example. It should be noted that in general surgical navigation systems are configured to register objects to an arbitrary coordinate space such as the common coordinate space described above.

Figure 3:
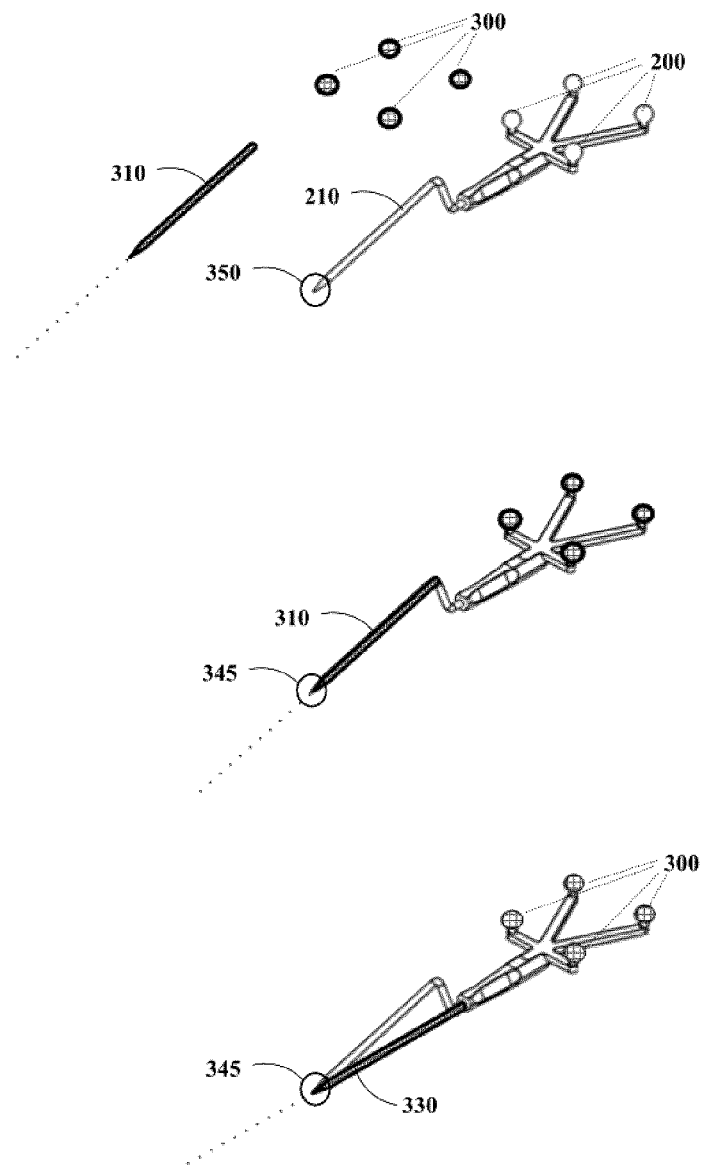
FIG. 3 illustrates a typical surgical navigation system pointer tool used in registration.

In FIG. 3 a surgical instrument 210 is shown with its associated tracking markers (or landmarks) 200 and its associated virtual object representation comprised of virtual tracking markers (or landmarks) 300 and virtual pointer segment 310.

The surgical instrument 210 may be tracked with one or more sensors which are in communication with one or more transceiver(s) of the tracking system that receives, records and/or processes the information regarding the instrument(s) that the sensor(s) are detecting. The sensors may track, among other things, the spatial position of the instrument(s), including its angle and orientation (i.e. pose).

Active or passive actual tracking markers or landmarks locatable by the tracking system component of the surgical navigation system may be placed on the port 100 and/or imaging sensor 104, and/or any medical instruments to determine the location of these objects in the tracking coordinate space.

Exemplary tracking markers or landmarks (such as 200 shown in FIG. 2) may be IR reflective spheres configured to be seen by an IR stereo camera of an optical tracking system. In the same exemplary embodiment a tracked instrument tracked by the optical tracking system 113 is typically defined by a grouping of markers such as markers 200 of instrument 210, which may identify an arbitrary representative volume, and are used to determine the spatial position and orientation of the volume of the tracked instrument within the common coordinate space. Typically, in known exemplary optical tracking systems a minimum of three spheres are required on a surgical instrument to define the instrument's spatial position and orientation; however it is known in the art that the use of four markers is preferred. For example tool 210 shown in FIG. 2 uses four (4) optical tracking markers 200. An optical tracking system fitting the aforementioned description is the "Polaris" system available from Northern Digital Inc.

Using this system, differentiation of the tracked medical instruments and other objects and their corresponding virtual geometric volumes can be determined by the specific orientation of the reflective spheres relative to one another. These orientations would provide each virtual object an individual identity within the navigation system. Allowing the navigation system to identify the medical instrument or object and its corresponding virtual 3D representation. For example as shown as 310 in FIG. 3. The orientation of the tracking markers or landmarks also provide other useful information to the navigation system, such as the medical instrument or objects central point, the medical instrument or objects central axis and its orientation, and other information related to the medical instrument or object.

Alternative types of tracking markers or landmarks may include radio frequency (RF), electromagnetic (EM), pulsed and un-pulsed light emitting diodes (LEDs), glass spheres, reflective stickers, unique structures and patterns. Further, the RF and EM tracking markers or landmarks may have specific signatures for the specific tools they would be attached to. The reflective stickers, structures and patterns, glass spheres, LEDs could all be detected using optical detectors, while RF and EM could be picked up using antennas. Advantages to using EM and RF tags would include exemption of the line-of-sight restriction during the operation, whereas advantages to using an optical tracking system would be the alleviation of additional noise and distortion from environmental influences inherent to electrical emission and detection systems.

In a further embodiment, 3-D design markers could be used for detection by an auxiliary camera and/or optical imaging system. Such markers could also be used as a calibration pattern to provide distance information (3D) to the optical detector. These identification markers may include designs such as concentric circles with different ring spacing, and/or different types of bar codes. Furthermore, in addition to using markers, the contours of known objects (i.e., side of the port) could be made recognizable by the optical imaging devices through the tracking system.

Creation of a Common Coordinate Space

The common coordinate space may be composed of both an actual coordinate space and a virtual coordinate space, where the actual coordinate space contains actual objects that exist in space and the virtual coordinate space contains virtual objects that are generated in a virtual space. The common coordinate space containing both the aforementioned actual and virtual objects may be produced as follows.

Figure 4:
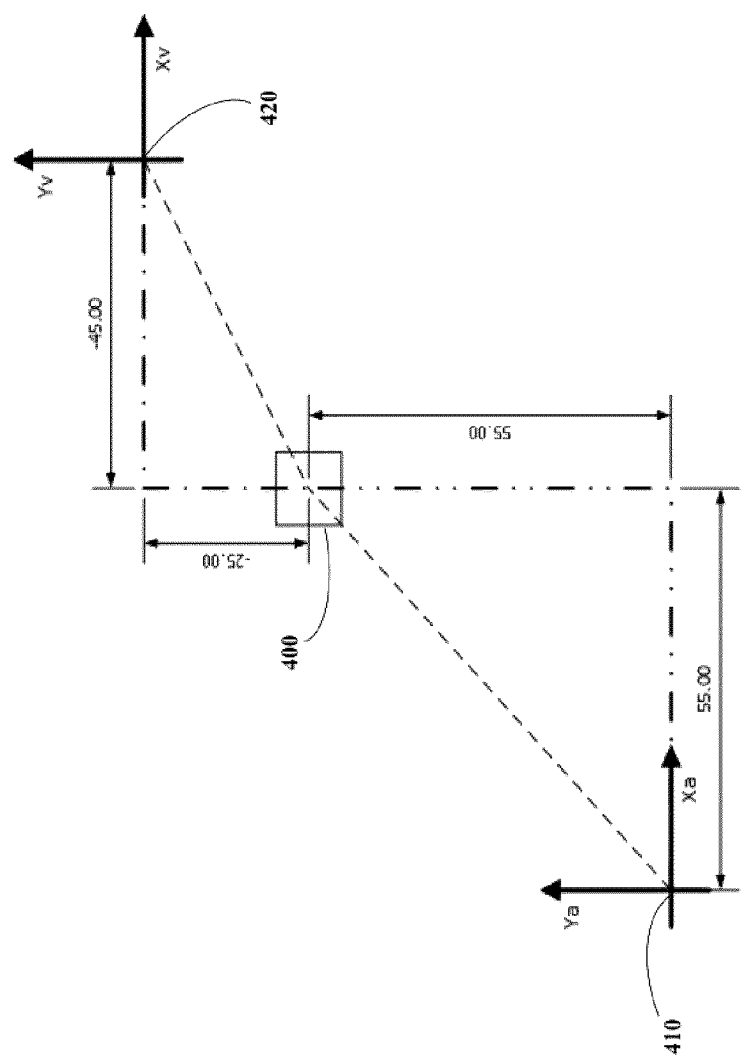
FIG. 4 is a diagram illustrating a registration process.

In order to form a common coordinate space composed of the amalgamated virtual and actual coordinate spaces, the two spaces must be coupled with a "common reference coordinate", having a defined position that can be located in both the actual and virtual coordinate spaces. An example of such a common reference coordinate 400 and actual and virtual coordinate space origins, 410 and 420, are provided in FIG. 4. Once the common reference coordinate position is acquired in both spaces they can be used to correlate the position of any point in one coordinate space to the other. The correlation is determined by equating the locations of the common reference coordinate in both spaces and solving for an unknown translation variable for each degree of freedom defined in the two coordinate spaces. These translation variables may then be used to transform a coordinate element of a position in one space to an equivalent coordinate element of a position in the other. An example correlation can be derived from the diagram in FIG. 4 depicting a two dimensional coordinate space. In the figure the common reference coordinates 400 position is determined relative to the actual coordinate space origin 410 and the virtual coordinate space origin 420. The common reference coordinates positions can be derived from the diagram as follows:

$$(X_{cra}, Y_{cra}) = (55, 55)$$

and $$(X_{crv}, Y_{crv}) = (-25, -45)$$

Where the subscript "cra" denotes the common reference coordinate position relative to the actual coordinate space origin and the subscript "crv" denotes the common reference coordinate position relative to the virtual coordinate space origin. Utilizing a generic translation equation describing any points $((Y_a, X_a)$ and $(Y_v, X_v))$, where the subscript "a" denotes the coordinates of a point relative to the actual coordinate space origin 410, and the subscript "v" denotes the coordinate of a point relative to the virtual coordinate space origin 420, we can equate the individual coordinates from each space to solve for translation variables $((Y_T, X_T))$, where the subscript "T" denotes the translation variable as shown below.

$$Y_a = Y_v + Y_T$$

$$X_a = X_v + X_T$$

Now substituting the derived values of our points from FIG. 4 we can solve for the translation variable.

$$55 = -45 + Y_T$$

$$100 = Y_T$$

and $$55 = -25 + X_T$$

$$80 = X_T$$

Utilizing this translation variable, any point ((i.e. $(Y_v, X_v)$) in the virtual coordinate space may be transformed into an equivalent point in the actual coordinate space through the two generic transformation equations provided below. It should be noted that these equations can be rearranged to transform any coordinate element of a position from the actual coordinate space into an equivalent coordinate element of a position in the virtual coordinate space as well.

$$Y_a = Y_v + 100$$

and $$X_a = X_v + 80$$

This will allow both the virtual and actual objects respective positions to therefore be defined in both the actual and virtual coordinate spaces simultaneously. Once the correlation is determined the actual and virtual coordinate spaces become coupled and the result in the formation of a common coordinate space that may be used to register virtual and actual object. It should be noted that these virtual and actual objects can be superimposed in the common coordinate space (i.e. they can occupy the same coordinates simultaneously).

The Patient Reference Marker

The "common reference coordinate" as described above may be any object that can be located within both the actual and virtual coordinate spaces. In the case of the exemplary optical tracking system mentioned above, IR reflecting tracking markers are locatable in both coordinate spaces allowing any IR reflecting marker to act as a common reference coordinate. In typical surgical procedures employing a surgical navigation system the standard is to employ a static optical tracking marker, termed the "Patient Reference Marker" to act as the common reference coordinate. For the purposes of this disclosure all common reference coordinates as defined above will be referred to as Patient Reference Markers. It should be noted that the Patient Reference Marker is referred to as the "reference frame" in the paper [The Silent Loss of Navigation Accuracy; Research-Human-Clinical Studies; Vol. 72, No. 5, May 2013, pages 796-807] mentioned above.

It should be noted that the terms coordinate frame and coordinate space may be used interchangeably throughout this disclosure and within the incorporated references Two (2) Types of Registration Once the common coordinate space is established, all objects in it are then defined by their position relative to the Patient Reference Marker. There are two sets of objects that can be registered to the common coordinate space by the navigation system. The first set are virtual objects that are statically registered to the common coordinate space using landmarks, such as patient imaging. The second set are virtual objects that are dynamically registered to the common coordinate space using tracking markers. Static registration is commonly done using a multitude of methods the most common being a touch-point registration and a surface scan registration as described in the patent application CA/2014/050266, titled "SYSTEM AND METHOD FOR DYNAMIC VALIDATION, CORRECTION OF REGISTRATION FOR SURGICAL NAVIGATION" incorporated in its entirety herein by reference. Static registration can be done by identifying landmarks as positions in the common coordinate space using a tracked medical instrument with a corresponding 3D volume. In a particular example such as that depicted in FIG. 3 the position of the tip 345 of the 3D volume may be used to identify the coordinate of a point to be used in a touch point registration. Dynamic registration is known in the art and in some implementations is referred to as tracking. A full description of dynamic registration is described in the patent application CA/2014/050767, titled "SYSTEM AND METHOD FOR PROJECTED TOOL TRAJECTORIES FOR SURGICAL NAVIGATION SYSTEMS" incorporated in its entirety herein by reference. Dynamic registration involves periodically registering a landmarks such as tracking markers to the common coordinate space. When this periodic registration is done at such a high frequency that the registration seems continuous it is known in the art as tracking. When defined in the common coordinate space the landmarks such as tracking markers may be used to identify a 3D volume that also has representative position relative to the landmarks in the common coordinate space. FIG. 3 shows two exemplary 3D volumes for surgical instrument 210 composed of sections 300 and 310 and sections 300 and 330 respectively. Both depicted 3D volumes have the same coordinates for the tip 345 of their respective pointers relative to their tracking markers 300. When registered to the common coordinate space the tip 345 of the 3D volume defines the actual location of the tip 350 of the actual surgical instrument 210 in the common coordinate space.

It should be noted that tracking markers are a type of landmarks in that they define a position in space, but are a unique set of landmarks in that they are visible to a specific tracking system, whereas other landmarks may not be. Regardless of the type all landmarks may be used to register objects to the common coordinate space as described above. Landmarks may be embodied in various forms for surgical procedures such as, vertices, anatomical depressions, anatomical protrusions, arbitrarily defined points, translated points, etc.

Multiple Common Reference Coordinates

Figure 5:
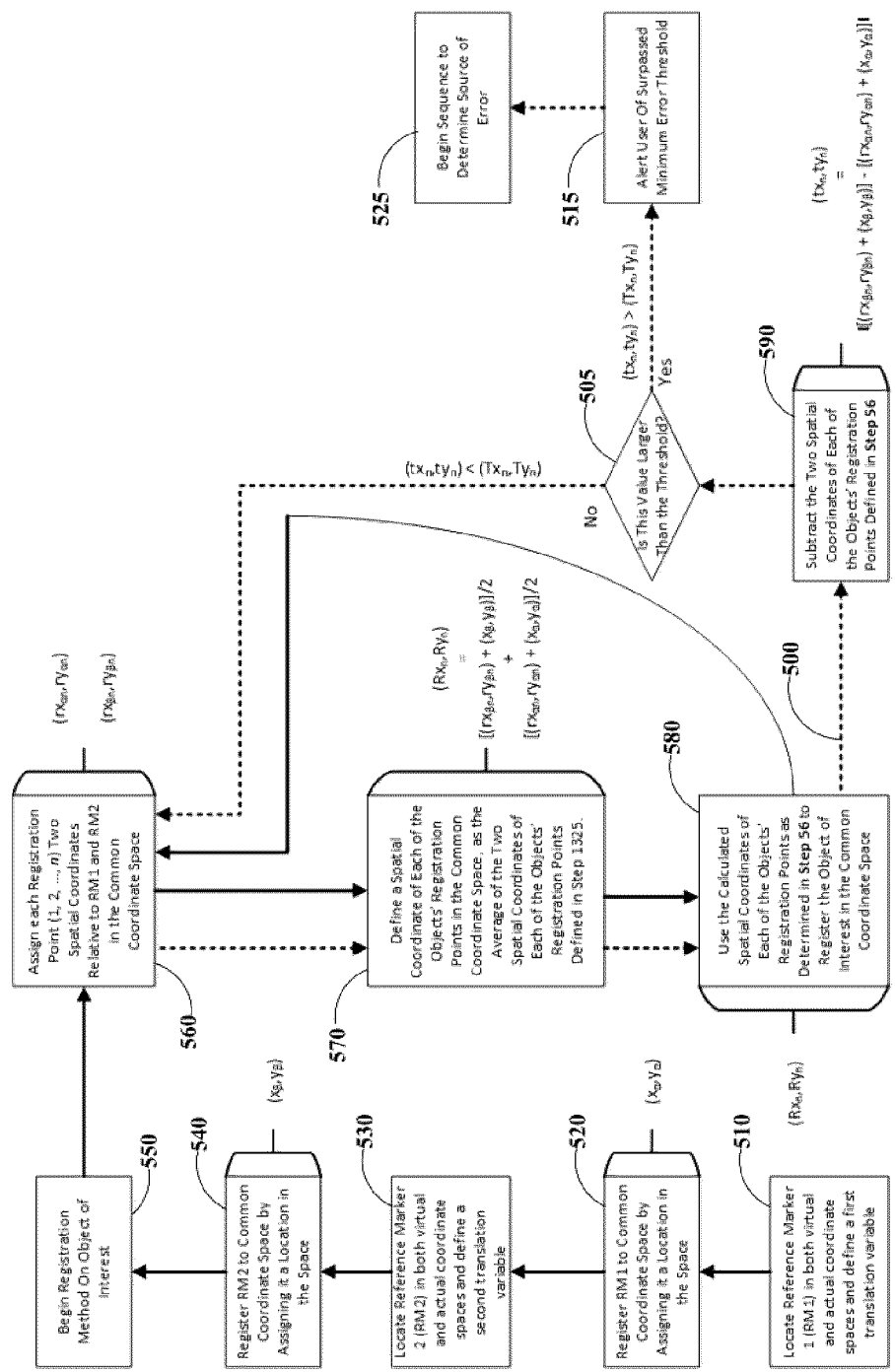
FIG. 5 illustrates a flow chart describing the use of multiple Patient Reference Markers for registration.
Figure 6:
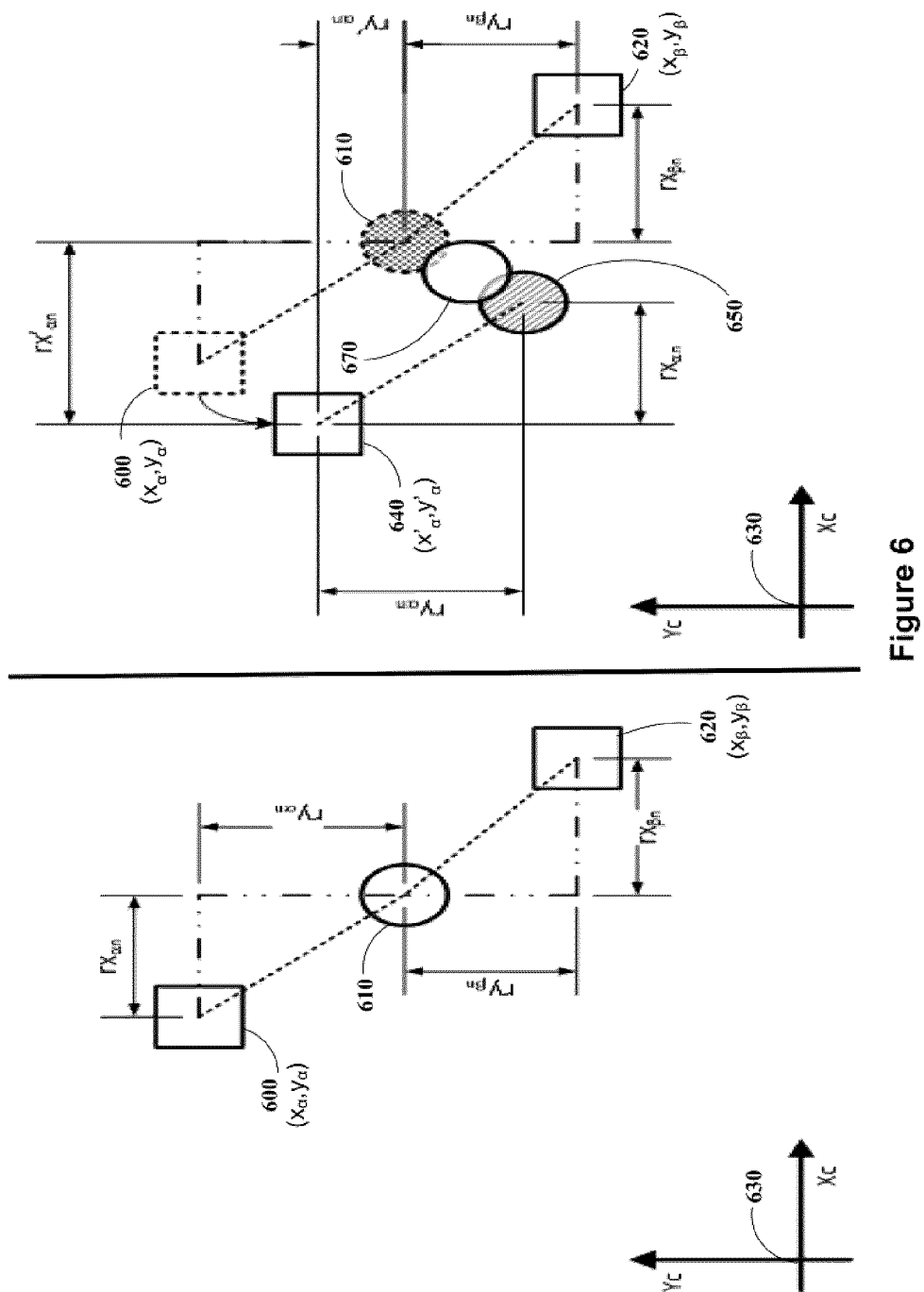
FIG. 6 illustrates a diagram describing the use of multiple Patient Reference Markers for registration of objects.

Although not commonly practiced in industry it may be possible improve registration accuracy by using multiple Patient Reference Markers such as 600 and 620 shown in FIG. 6. The use of multiple Patient Reference Markers is described in detail in the patent application CA/2014/050266, titled "SYSTEM AND METHOD FOR DYNAMIC VALIDATION, CORRECTION OF REGISTRATION FOR SURGICAL NAVIGATION" already incorporated in its entirety by reference. For the purposes of clarity in this disclosure the general concept of using multiple references is reiterated in FIG. 5 as a flow chart and a complimentary explanatory diagram shown in FIG. 6. This flow chart describes the use of two Patient Reference Markers which are used to periodically register (dynamically and statically) objects to the common coordinate space shown as 630. Steps 510-540 involve locating both Patient Reference Markers, RM1 and RM2, shown as 600 and 620 in the left frame of FIG. 6, and calculating their respective translation variables to create the coupled common coordinate space as described above. Each Patient Reference Marker will have a registered position in the common coordinate space relative to the origin 630 and shown in FIGS. 5 and 6 as $$(x_\alpha, y_\alpha) \text{ and } (x_\beta, y_\beta)$$

Where the subscript $\alpha$ denotes that the coordinate is used to define the first Patient Reference Marker and the subscript $\beta$ denotes that the coordinate is used to define the second Patient Reference Marker. Once registration begins 550 each landmark, shown as 610 in the left frame of FIG. 6, is assigned a coordinate in the common coordinate space 560 relative to each of the Patient Reference Markers. These assigned coordinates are shown in both FIGS. 5 and 6 in 2D as $$(rx_{\alpha n}, ry_{\alpha n}) \text{ and } (rx_{\alpha n}, ry_{\alpha n})$$

Where the prefix r denotes that the coordinate defines the position of the $n^{th}$ landmark as a vector extending to it from the respective Patient Reference Marker. The subscript αn denotes that the variable is used to define the $n^{th}$ landmarks relative coordinate to the first Patient Reference Marker, and the subscript βn denotes that the variable is used to define the $n^{th}$ landmarks relative coordinate to the second Patient Reference Marker. Next the landmarks are registered to the common coordinate space (step 580) at a coordinate defined as the calculated average of the $n^{th}$ landmarks' respective coordinates relative to each of the Patient Reference Markers 570 (only two in this scenario). This calculated coordinate is depicted in FIG. 5 and calculated as follows $$(Rx_n, Ry_n) = [(rx_{\beta n}, ry_{\beta n}) + (x_\beta, y_\beta)]/2 + [(rx_{\alpha n}, ry_{\alpha n}) + (x_\alpha, y_\alpha)]/2$$

Where the prefix R indicates that this coordinate is an average of the coordinates of the $n^{th}$ landmarks position relative to all the respective Patient Reference Markers (Patient Reference Markers α (RM1) and β (RM2) in this example). Steps 570, 580, and 560 form a loop that periodically re-registers the landmarks to the common coordinate space after updating the coordinates of the landmarks. In an embodiment this periodic registration may be updated at a high enough frequency such that the registration seems continuous and again, may be referred to as tracking. The right frame of FIG. 6 depicts an exemplary scenario which will be described in further detail below.

The flow chart in FIG. 5 also contains an additional loop that is distinguishable by dashed arrows 500 describing added steps that may be used to confirm accurate registration. After registering the n landmarks (that may collectively define an object) to the common coordinate space a test variable is calculated by taking the absolute difference in position of each of the landmarks' coordinates in the common coordinate space as defined relative to each of the two Patient Reference Markers (step 590). This is shown in FIG. 5 as:

$$(tx_n, ty_n) = |[(rx_{\beta n}, ry_{\beta n}) + (x_\beta, y_\beta)] - [(rx_{\alpha n}, ry_{\alpha n}) + (x_\alpha, y_\alpha)]|$$

Where the prefix t denotes that the coordinate value is a test variable. This test variable is than tested to see if it's greater than a minimum threshold (step 505). If it is found to be greater than the threshold, shown in FIG. 5 as:

$$(tx_n, ty_n) > (TX_n, Ty_n)$$

Where the prefix T denotes that this coordinate is a threshold variable. Then the surgeon is warned (step 515) of the inaccuracy and a sequence may be implemented to try and determine the source of the error (step 525) which will be described further below. If the test variable is lower than the minimum threshold, shown in FIG. 5 as $$(tx_n, ty_n) < (Tx_n, Ty_n)$$

Then than the landmarks (or collectively the object) coordinates are updated (step 560) and the loop consisting of registering the n landmarks (or collectively an object) and verifying the accuracy of their registration repeats. In addition it should be noted that the 2D examples shown above may be expanded to 3D, 4D, and higher such as 6DOF systems.

Determining a Moved Reference (Generic)

Surgical navigation systems which employ multiple Patient Reference Markers have the inherent characteristic that they may be analyzed to infer whether there exists an error in accuracy and if so, the source of that error. This is unlike commonly employed surgical navigation systems which employ only a single Patient Reference Marker and therefore lack this inherent characteristic. The use of two or more Patient Reference Markers allows for the determination of an error while the use of three or more Patient Reference Markers enables the system to potentially infer the source of an error in addition to detecting that error. By employing multiple Patient Reference Markers a scenario is created in which the expected coherence of registered landmark positions can be verified as they are defined relative to multiple Patient Reference Markers simultaneously. By determining which calculated landmark positions remained coherent (similar) and which ones deviate from the expected coherence, it may be probabilistically inferred that the coordinates which deviated were calculated using inaccurately registered Patient Reference Markers. As will be elaborated further below.

Navigation System Components

In general, surgical navigation systems consist of objects and means of locating those objects relative to at least one Patient Reference Marker. These objects may be actual objects such as surgical instruments or virtual objects such as patient scans. The means on the other hand are generally sensors which acquire the location of the objects. The locating of objects using surgical navigation systems, thus relies on two main hardware components; the systems sensors and the Patient Reference Marker(s). These hardware components may be employed in varying combinations of sensors and Patient Reference Markers to optimize surgical navigation system design and viability as discussed further below.

Figure 7:
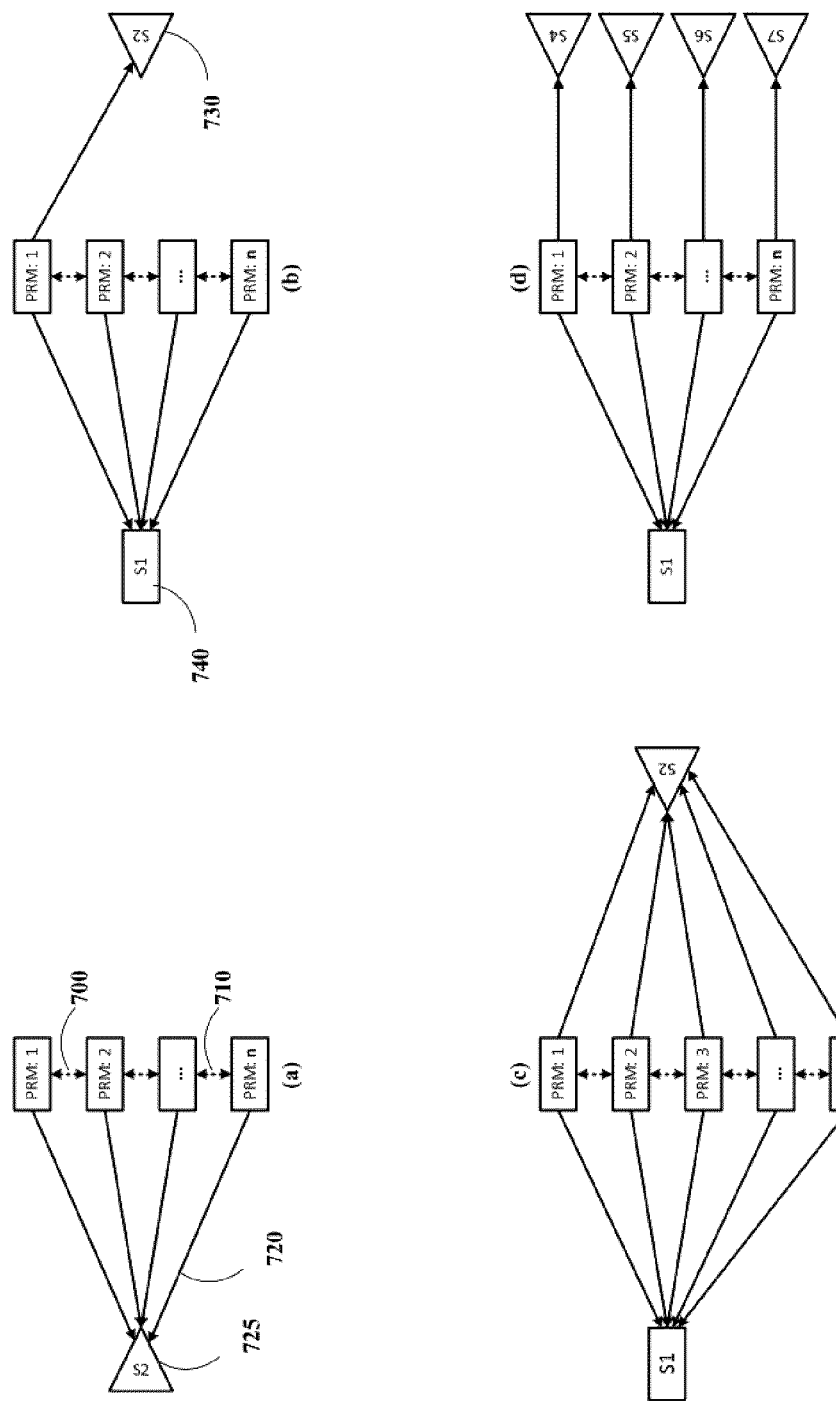
FIG. 7 illustrates varying surgical navigation system configurations.

FIG. 7 depicts surgical navigation systems with varying possible combinations that may be used, in the figure prefix' S denote sensors and prefix' PRM denote Patient Reference Markers. The first scenario (a) shown in FIG. 7 has a single sensor and multiple Patient Reference Markers.

Figure 8:
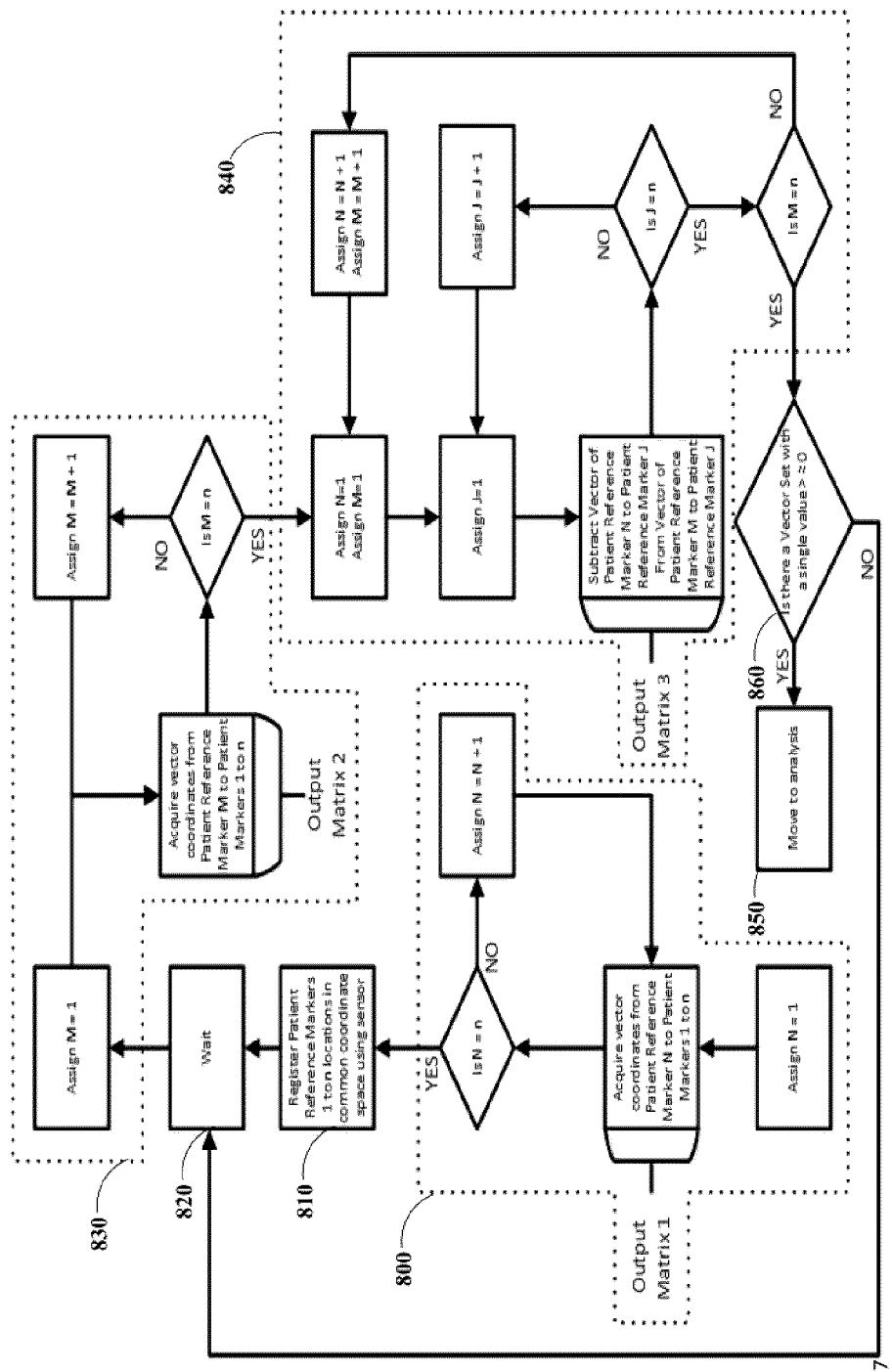
FIG. 8 illustrates a flow chart describing how to detect for accuracy error.

FIG. 8 depicts a flow chart describing an exemplary way in which a surgical navigation system may acquire a differential vector set from the onset of a surgery that may be subsequently utilized to determine the source of an error in a surgical navigation system. This flow chart may be applied to the first scenario (a) depicted in FIG. 7 as described as follows.

In the first section of the flow chart 800 in FIG. 8 before registration of the Patient Reference Markers to the common coordinate space each Patient Reference Markers position relative to all of the other Patient Marker References employed by the surgical navigation system are determined in the form of a vector and outputted into matrix 1 as shown here:

$$\text{Matrix } 1 = \begin{bmatrix} \vec{V}_{i1\ 1} & \cdots & \vec{V}_{i1\ n} \\ \vdots & \ddots & \vdots \\ \vec{V}_{iN\ 1} & \cdots & \vec{V}_{iN\ n} \end{bmatrix}$$

Where the subscript i of vector $\vec{V}_{ix\ y}$ denotes that the vectors were acquired at the time of initial registration, where the subscript f of vector $\vec{V}_{fx\ y}$ denotes that the vectors were acquired at a time after initial registration, and the subscripts x y denote that the vector is acquired by subtracting coordinates of Patient Reference Marker y from Patient Reference Marker x. It should be noted that this notation will be used throughout the remainder of this disclosure when referring to the vectors acquired from differences in position of the Patient Reference Markers. An exemplary vector $\vec{V}_{i1\ 2}$ 700 is shown in scenario (a) in FIG. 7. This vector has its origin at PRM: 2 and extends to PRM: 1. In this scenario the sensor S2 acquires the positions of all of the Patient Reference Markers (i.e. PRM: 1 . . . PRM: n) and can then determine the position of each of them relative to the rest 700, 710. It should be noted that there are vectors that will be acquired that are not shown in the figure. For example a vector from PRM: n to PRM: 1. Once Matrix 1 is acquired the Patient Reference Markers are registered to the common coordinate space (step 810). The next step is to wait a predetermined time (step 820) before continuing with the process. In the second major section 830 of the flow chart each Patient Reference Markers position relative to all of the other Patient Marker References are again determined (after the predetermined wait time 820) in the form of a vector and outputted into matrix 2 as shown here:

$$\text{Matrix 2} = \begin{bmatrix} \vec{V}_{i1\ 1} & \cdots & \vec{V}_{i1\ n} \\ \vdots & \ddots & \vdots \\ \vec{V}_{iM\ 1} & \cdots & \vec{V}_{iM\ n} \end{bmatrix}$$

Matrix 2 shows the positions of all the Patient Reference Markers relative to all the other Patient Reference Markers at recurring time intervals after the Patient Reference Markers have been initially registered. In the final section 840 of the flow chart the absolute differences in positioning between the time of registration and after a given time interval of the Patient Reference Markers relative to all of the other Patient Reference Markers are calculated and output as a matrix shown here:

$$\text{Matrix 3} = \begin{bmatrix} |\vec{V}_{i1\ 1} - \vec{V}_{f1\ 1}| & \cdots & |\vec{V}_{i1\ n} - \vec{V}_{f1\ n}| \\ \vdots & \ddots & \vdots \\ |\vec{V}_{iN\ 1} - \vec{V}_{fM\ 1}| & \cdots & |\vec{V}_{iN\ n} - \vec{V}_{fM\ n}| \end{bmatrix}$$

$$\text{Matrix 3} = \begin{bmatrix} \vec{V}_{1\ 1} & \cdots & \vec{V}_{1\ n} \\ \vdots & \ddots & \vdots \\ \vec{V}_{N\ 1} & \cdots & \vec{V}_{N\ n} \end{bmatrix}$$

Matrix 3 shows any relative changes in positioning of the Patient Reference Markers between the time of registration and an elapsed time interval. Each row of the matrix is a vector set which represents the $N^{th}$ Patient Reference Markers differential vectors with respect to all of the other Patient Reference Markers.

In an ideal surgical procedure all of the relative positions of the Patient Reference Markers relative to one another would remain constant (not move) throughout the procedure. However realistically minor shifts in position occur commonly. Mapping out the relative shift of a Patient Reference Marker against all of the other Patient Reference Markers allows us to monitor the position of that Patient Reference Marker in a manageable manner. If a Patient Reference Marker's position shifts relative to the rest of the Patient Reference Markers, while the rest stay in the same position relative to one another excluding the one which has shifted, it may be probabilistically inferred that any detected error in the system should be attributed to the Patient Reference Marker with the shifted position relative to the rest. This is because the probability of the rest of the Patient Reference Markers shifting in a consistent manner, such that all of their positions relative to one another remain constant, excluding the one Patient Reference Marker with a shifted relative position to the rest, is highly unlikely compared to the alternative. The alternative being that the one Patient Reference Marker with a shifted position relative to the rest has actually shifted in position. After acquiring matrix 3 the next step in the flow chart is to check each vector set (row of the matrix from $\vec{V}_{N\ 1} \rightarrow \vec{V}_{Nn}$) from Patient Reference Marker N=1 to N=n for a single element which is not approximately a zero value excluding values along the diagonal of the matrix. If an approximate non-zero value element is found then accuracy error is present in the surgical navigation system and the system continues to the next stage (850) to attempt to infer the source of the error. However if no approximate non-zero elements are found then the system loops back to the wait step 820 until enough time elapses and the flow chart can again check the accuracy of the system.

Figure 9:
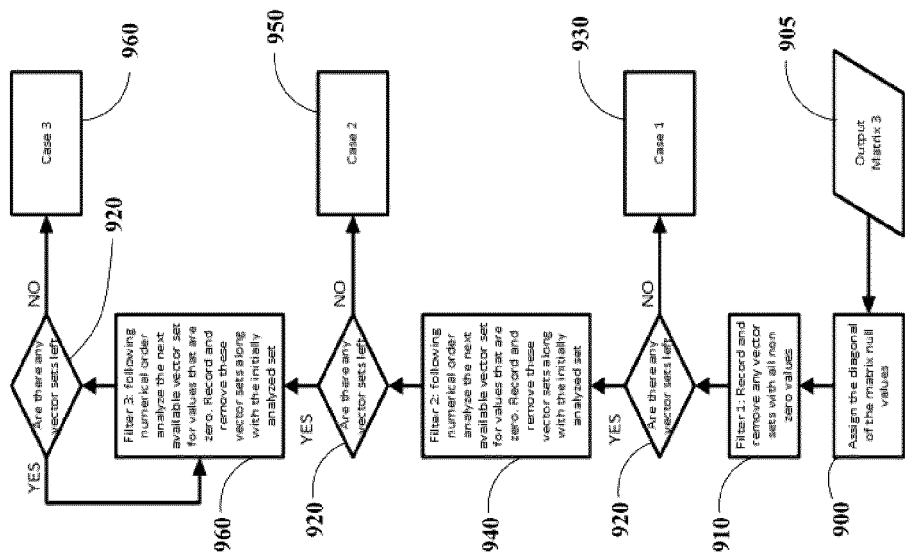
FIG. 9 illustrates a flow chart describing how to determine the source of an accuracy error.

A flow chart showing an exemplary analysis of the elements of the vector sets in matrix 3 executable by the surgical navigation system is shown in FIG. 9. Starting with the output matrix 3 905, as shown above, each diagonal element in the matrix is assigned a null value (no entry) 900. In the following steps of the flow chart the matrix is put through a set of filters that group the Patient Reference Markers depending on their positions relative to other Patient Reference Markers. The first filter 910 records and removes any vector sets (each set corresponding to a particular Patient Reference Marker) containing no elements with an approximately zero value from matrix 3 (i.e. remove vector sets in which all values are non-zero). These vector sets are removed because the Patient Reference Markers associated with these vector sets can be assumed to have shifted position and therefore need re-registration.

Once the first filter is passed the next step is to determine if any vector sets remain 920. If not then this means a Case 1 930 has occurred and it can be probabilistically inferred all of the Patient Reference Markers of the respective surgical navigation system have shifted and therefore need to be re-registered. However If any vector sets remain they must be analyzed to determine whether or not their associated Patient Reference Markers have shifted (step 920). The second filter 940 analyzes the contained elements in the next available vector set following numerical order. The elements of this vector set which have an approximate value of zero will be recorded and the vector sets corresponding to those elements (i.e. the Patient Reference Marker corresponding to the column that element is in) will be removed along with the vector set being analyzed.

The Patient Reference Markers corresponding to the vector sets removed from the matrix have all conserved their position relative to the other Patient Reference Markers in these vector sets. Probabilistically then these Patient Reference Markers have likely not shifted position relative to their initial registered positions. Once this filter is passed the next step is to determine if any vector sets remain 920. If not then this means a Case 2 950 has occurred and it can be probabilistically inferred that all of the Patient Reference Markers corresponding to the vector sets that were removed in the second filter haven't shifted in position and are still accurate. If there are remaining vector sets then the matrix proceeds to filter three 960 which performs the same operation on the remaining matrix as filter two. Again the next available vector set following numerical order will be analyzed and the elements contained in the vector set which have an approximate value of zero will be recorded and the vector sets corresponding to those elements will be removed along with the vector set being analyzed.

The Patient Reference Markers corresponding to these vector sets have all conserved their position relative to the other Patient Reference Markers in these vector sets. Once this filter is passed if there are more vector sets the matrix is passed through this filter again in a loop until no vector sets remain and a Case 3 960 has occurred. Case 3 indicated that there are multiple groups of Patient Reference Markers in which each group contains Patient Reference Markers with positions that have remained constant relative to the rest of the Patient Reference Markers in that group. Although the positions within the group have been conserved (over the time interval) the positions of the Patient Reference Markers relative to Patient Reference Markers outside of the group have not been conserved. In this case assumptions such as, if one group is much larger than another, than it is less probable that the larger group has shifted in comparison to the probability that the smaller group had shifted, can be made and conclusions derived. The three cases mentioned here may be improved upon further with more effective and applicable configurations of sensors and Patient Reference Markers as will be discussed below. It should be noted that these vectors are not just distances but are position coordinates within a coordinate space.

Figure 10:
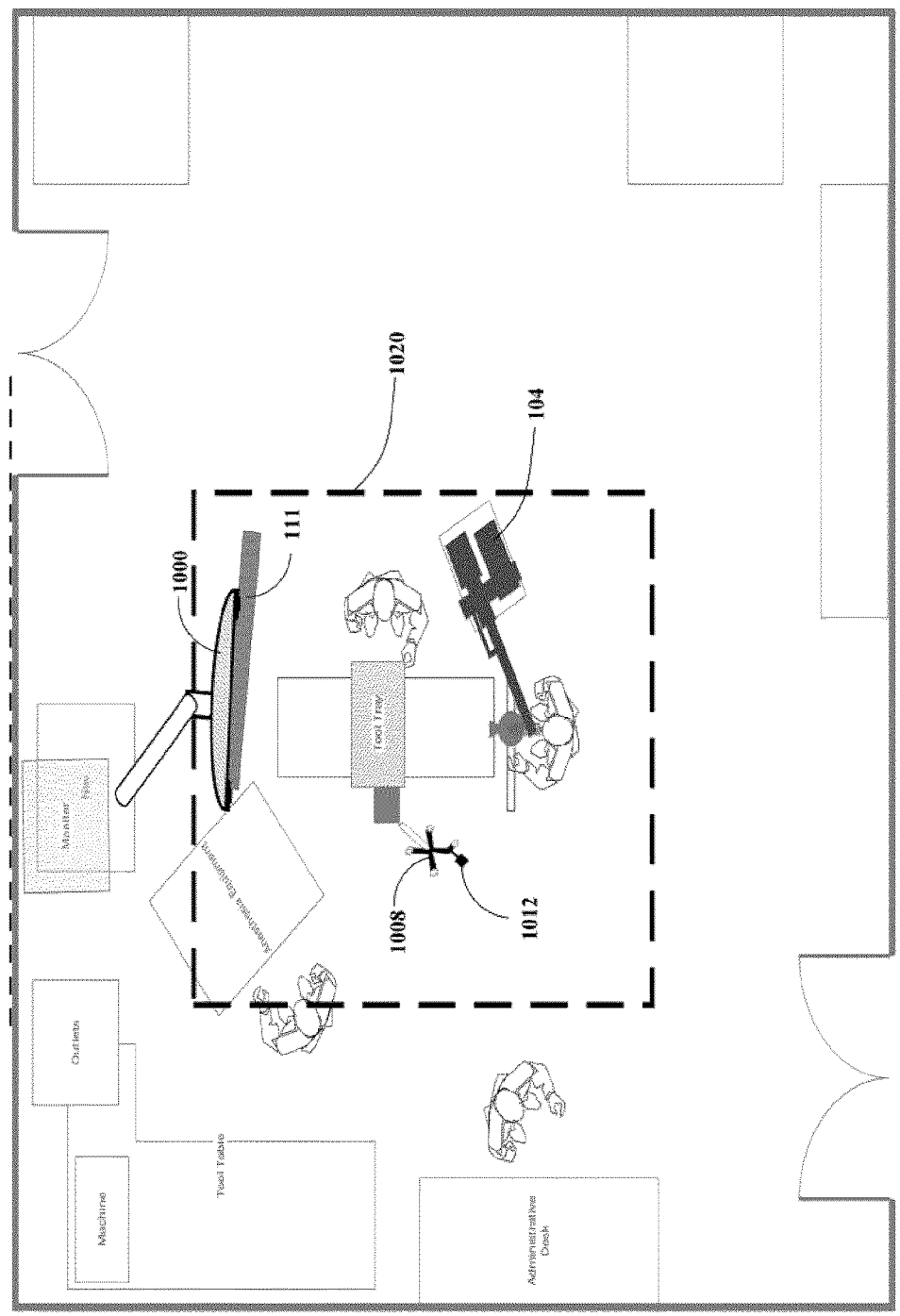
FIG. 10 illustrates a typical operating room setup.

FIG. 10 depicts an exemplary operating room set up for a brain tumor resection. The room includes a monitor 111 for displaying surgical information such as the navigation information indicating position of the objects in the common coordinate space. The room also includes a tracking sensor 1000 for registering objects in the common coordinate space, as well as a scope 104 such as a microscope or external video scope for viewing the surgical area of interest. The following figures focus on the area outlined by the barrier 1020 where multiple configurations of the surgical navigation system described above will be discussed.

Figure 11:
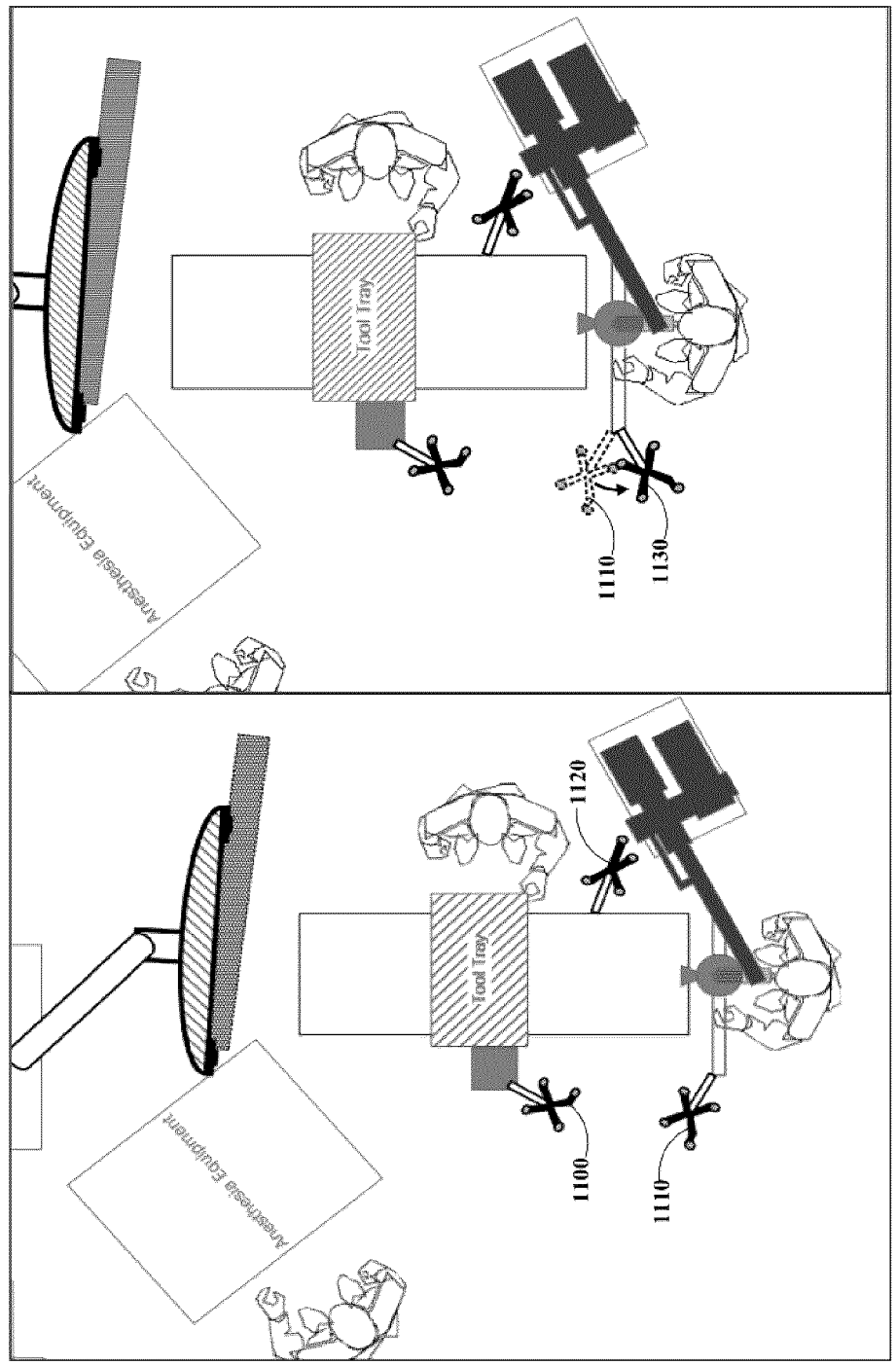
FIG. 11 illustrates an embodiment of a surgical navigation system employing three Patient Reference Markers.
Figure 12:
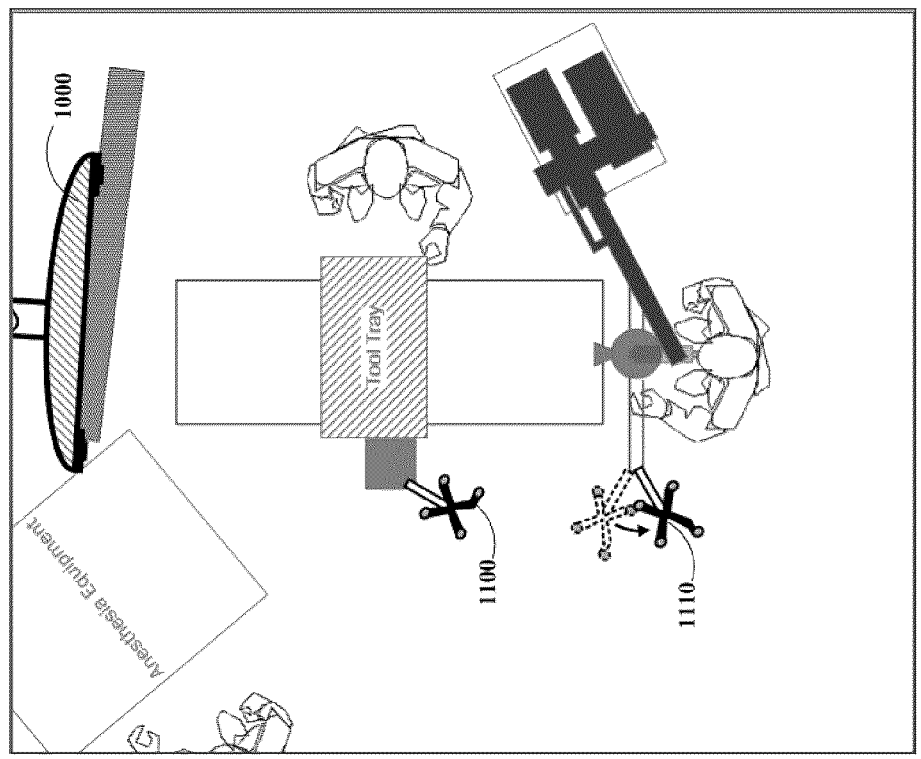
FIG. 12 illustrates an embodiment of a surgical navigation system employing two Patient Reference Markers.

FIGS. 11 and 12 depict practical embodiments of the surgical navigation configuration shown in section (a) of FIG. 7 where there is a single sensor and multiple Patient Reference Markers. In FIG. 11 the surgical navigation system employs three patient reference markers 1100, 1110, and 1120. The left frame of the figure shows the system when it is initially registered and the right frame shows the system after an elapsed time when a Patient Reference Marker has shifted position 1130. It is apparent that if the surgical navigation system executed the steps in the flow charts in FIGS. 8 and 9 as described above that an error would be detected and the source of that error would be determined to be a Case 2 where the only vector set with non-zero elements would correspond to Patient Reference Marker 1110 and therefore it would be deemed the source of the error. FIG. 12 is configured the same way as FIG. 11 only that instead of having an additional Patient Reference Marker, the surgical navigation system uses the sensor 1000 as a Patient Reference Marker.

It should be noted that when using the only sensor employed by a surgical navigation system as a Patient Reference Marker that this reference will be located at an origin with respect to all the other Patient Reference Markers. It should also be apparent from the above example that sensors which are employed by surgical navigation systems for registration may simultaneously be configured as Patient Reference Markers for dual use by that same surgical navigation system. In this particular case then the relative position of PRM: n to the sensor S2 725 in section (a) of FIG. 7 would be the vector 720.

Figure 13:
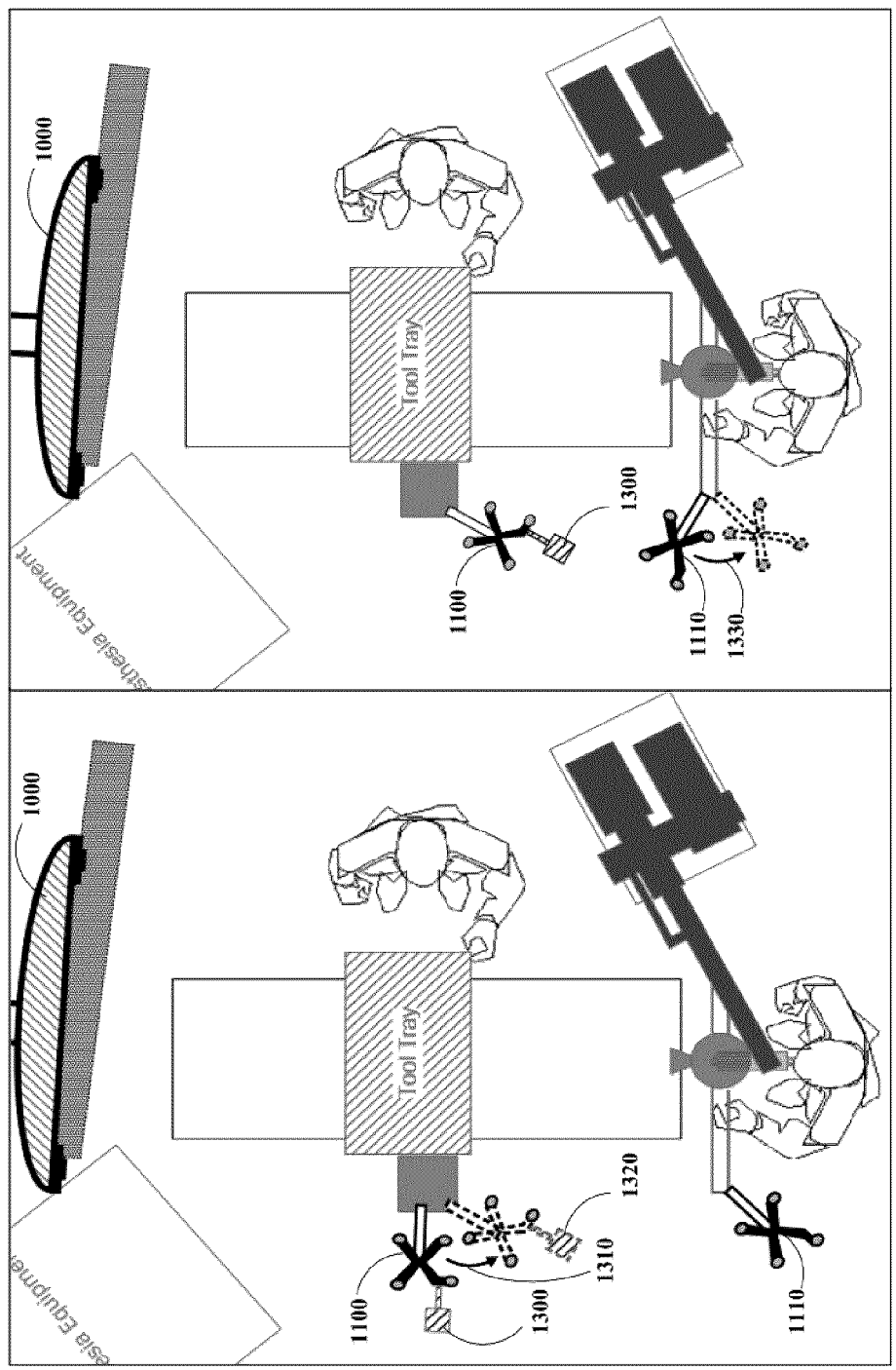
FIG. 13 illustrates an embodiment of a surgical navigation system employing a bump sensor.
Figure 16:
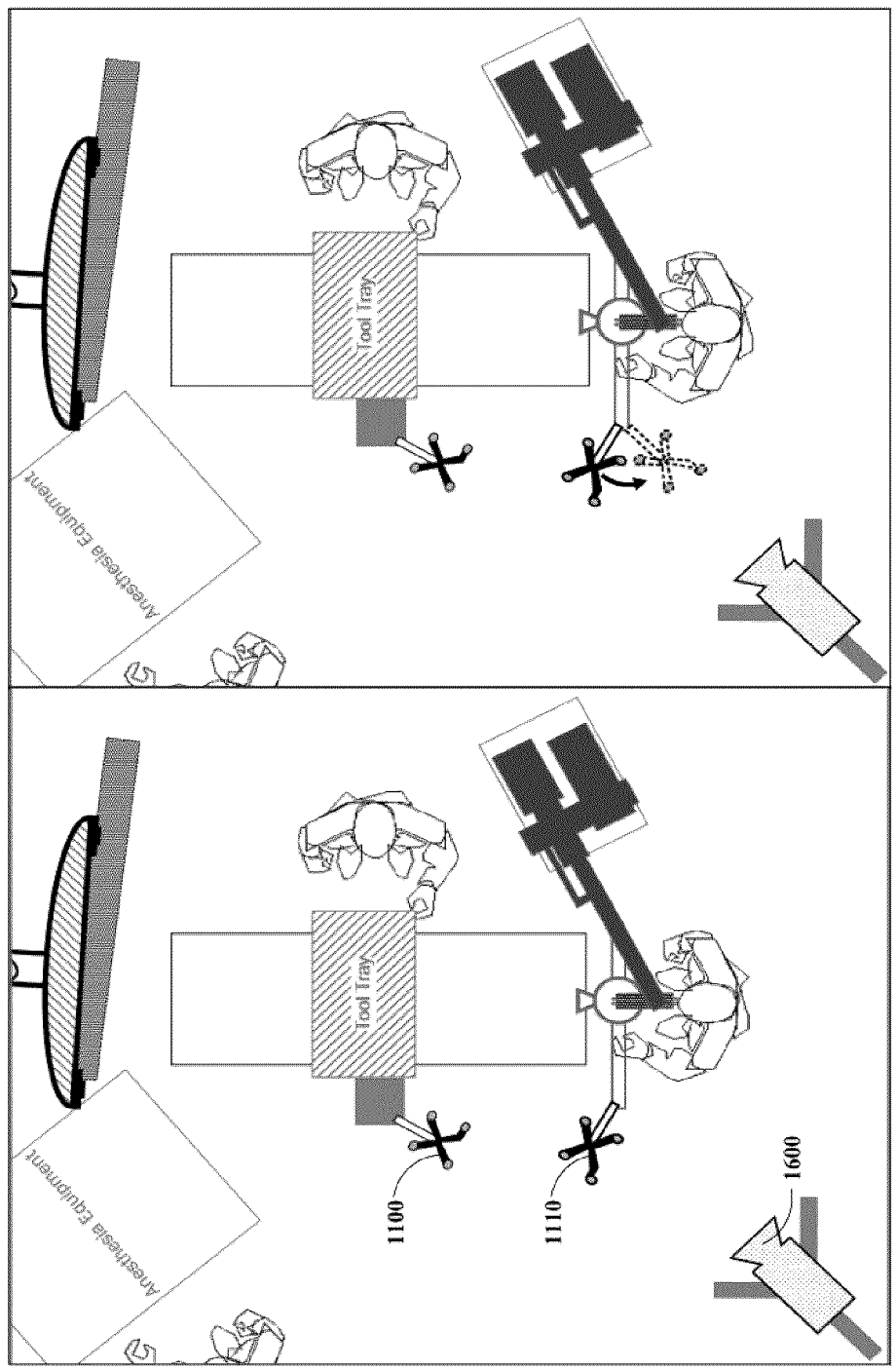
FIG. 16 illustrates an embodiment of a surgical navigation system employing an additional optical sensor.
Figure 17:
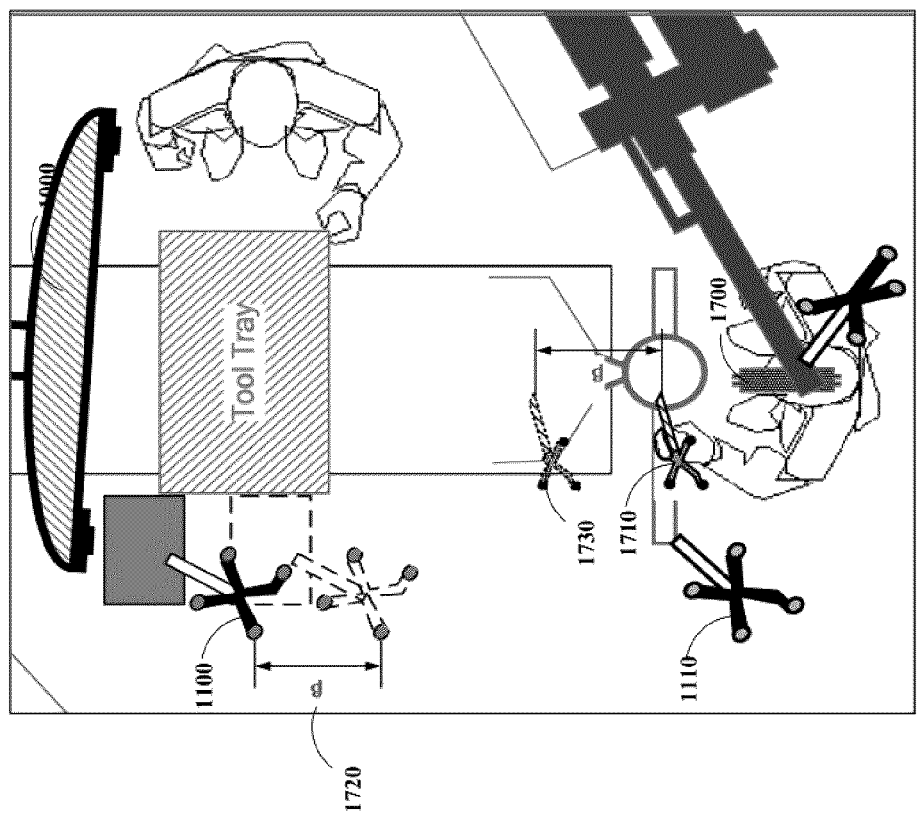
FIG. 17 illustrates an embodiment of a surgical navigation system employing a surgical scope sensor.

FIGS. 13, 16 and 17 depict practical embodiments of the surgical navigation configuration shown in scenario (b) of FIG. 7 where there are two sensors and multiple Patient Reference Markers. The sensor 730 has the specific characteristic in that it can only be used to monitor a single Patient Reference Markers position.

Using Attached Sensor as a Patient Reference Marker

In surgical navigation systems that only employ two Patient Reference Markers analysis of the system to determine the error through the use of the flow charts in FIG. 8 and FIG. 9 is ineffectual. In such a situation the sensor 730 can act as an additional reference marker such that the positions of the Patient Reference Markers in the system can be determined relative to it. In this way the sensor S2 730 may be employed for use as the third pseudo Patient Reference Marker in the flow charts in FIGS. 8 and 9 in that the sensors position at the time of and after registration can be used to form a row (vector set) in the output matrix 3 and used to analyze the system for the source of the error.

For clarity the sensor S2 730 may be employed as a pseudo Patient Reference Marker to produce a vector set as described in the flow charts in FIGS. 8 and 9 if it is used in the manner described as follows. In scenario (b) of FIG. 7 the sensors S2 730 position may be determined relative to a single Patient Reference Marker such as PRM: 1, for example denoted as $\vec{V}_{S2\,1}$. Then through vector addition its position may be determined relative to other Patient Reference Markers for example as shown here:

$$\vec{V}_{S2\,2} = \vec{V}_{S2\,1} + \vec{V}_{1\,2}$$

Or more generally $$\vec{V}_{S2\,y} = \vec{V}_{S2\,1} + \vec{V}_{1\,y}$$

Where the relative positions of the Patient Reference Markers are determined using the additional sensor in the system S1. Using the relative position of the sensor S2 730 and the principles of vector addition as described above the sensor can be used to form its own vector set in matrix 3 in the flow chart in FIG. 8 and subsequently used in the flow chart in FIG. 9. Although the sensor 730 may be employed as a pseudo Patient Reference Marker for analysis purposes it is not a Patient Reference Marker per se in that it is not used to register objects to the common coordinate space.

Using Attached Sensor with More than Two Patient Reference Markers

In surgical navigation systems that employ more than two Patient Reference Markers the sensor S2 730 may be used as an external information source to improve upon the analysis which determines the source of the error. In this situation the sensor may provide the surgical navigation system with information regarding the movement of the particular Patient Reference Marker which it is monitoring. For example if a Case 3 from the flow chart in FIG. 9 as described above were to occur, information regarding whether a particular Patient Reference Marker in one of the groups moved from the time it was registered to the time of analysis would allow for a conclusion to be reached about the state of that group. To further clarify a conclusion that the entire group remained accurately registered may be reached, if there was no detected movement by the sensor 730 of the particular Patient Reference Marker, and a conclusion that the entire group was inaccurately registered, if there was detected movement of the particular Patient Reference Marker.

The scenario above in which the sensor S2 730 is used as a pseudo Patient Reference Marker may also be used to improve the analysis of the system to determine whether an accuracy error exists and if so the source of that error. In this example the sensor may again provide the surgical navigation system with information regarding the movement of the particular Patient Reference Marker which it is monitoring. The difference being in this situation the movement is determined relative to the sensor 730 as it is being employed as a pseudo Patient Reference Marker and not just a detected movement of the particular Patient Reference in general.

Essentially when employing the additional sensor S2 730 it can be reasonably assumed that any detected movement is an accurate portrayal of the true movement of the monitored Patient Reference Marker from the time the monitoring began (the time of the last registration) to the time the analysis occurred. When assuming the detected movement is substantially representative of the true movement a necessary assumption is that the sensor position does not change. This means any movement of the Patient Reference Marker is determined by the Patient Reference Markers relative position to the position of the sensor S2 730 at the time when monitoring began. The position of the sensor S2 730 when the monitoring began is then necessarily a reference marker position identifying what the Patient Reference Marker has moved relative to. The reasoning behind whether it can be reasonably assumed that the detected movement of the Patient Reference Marker is true and consequently the sensor position has not shifted is a result of the choice of the type sensor, the positioning of the sensor in the operating room, and other considerations. Some examples of sensor S2 730 configurations and their use in scenario (b) of FIG. 7 are provided as follows.

Figure 15:
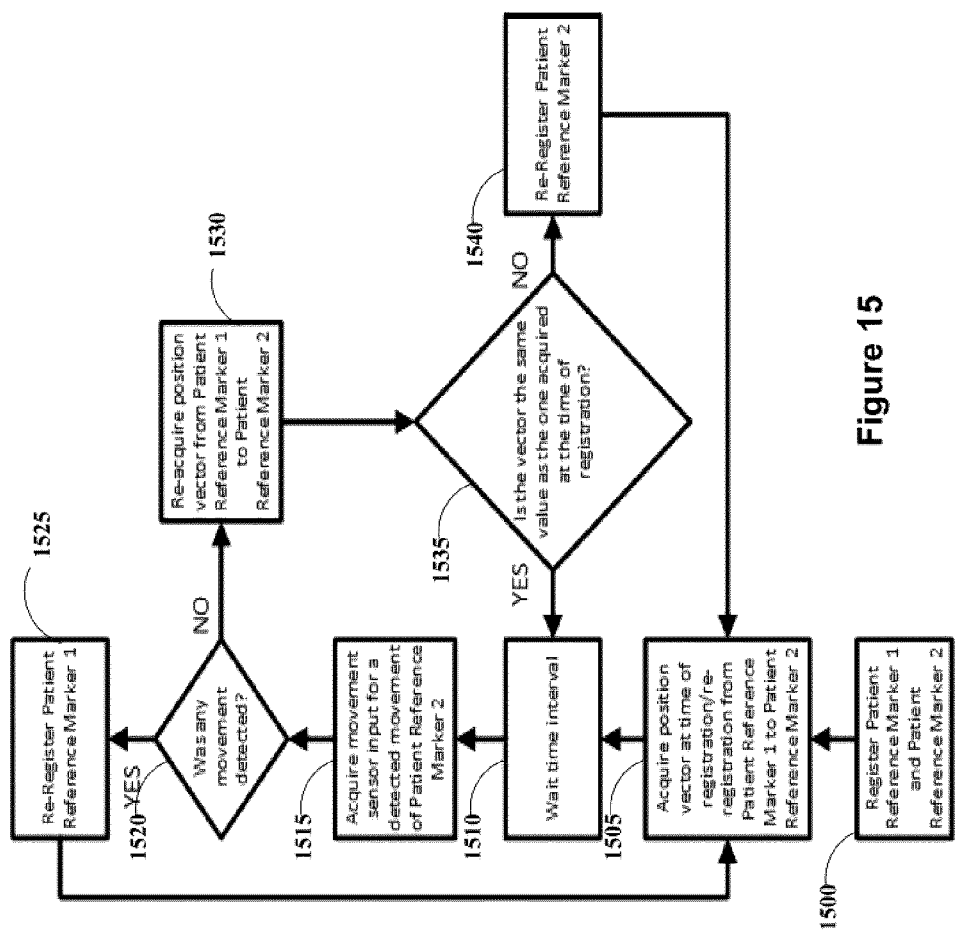
FIG. 15 illustrates a flow chart describing how to determine the source of an accuracy error when employing movement sensors.

In an embodiment depicted in FIG. 13 the surgical navigation system employs an optical sensor 1000 (S1), two optical Patient Reference Markers 1100 and 1110 locatable by the optical sensor, and a movement sensor 1300 (S2). The movement sensor can be an accelerometer, a gyroscope, etc. FIG. 13 depicts two scenarios in which inaccuracy is present. In the left frame the position of the Patient Reference Marker with the attached movement sensor is shifted, while in the right frame the position of the Patient Reference Marker without the attached movement sensor is shifted. The movement sensor 1300 provides an output to the surgical navigation system as to whether or not any movement of the Patient Reference Marker it is attached too was detected. In the left frame there are two Patient Reference Markers 1100 and 1110 and a movement sensor 1300 attached to Patient Reference Marker 1100. The scenario in this frame is equivalent to scenario (b) of FIG. 7 described in detail above in which there are two Patient Reference Markers and a sensor that may be employed as a reference marker. In the frame the sensors 1300 position at the time when monitoring begins is known relative to the Patient Reference Marker 1100. Its position relative to the second Patient Reference Marker 1110 may be calculated by the process described above. After a given time interval in this scenario the Patient Reference Marker 1100 shifts position as depicted by the arrow 1310. From the onset of the surgery depicted in this scenario the surgical navigation system will execute the flow chart shown in FIG. 8. Once the shift in position of the Patient Reference Marker 1100 occurs the surgical navigation system will then execute the flow chart in FIG. 9. The output matrix 3 acquired while executing the flow chart in FIG. 8 will be used as an input into the flow chart in FIG. 9. FIG. 14 depicts an example output matrix 3 for the embodiment depicted in the left frame of FIG. 13. The position of the Patient Reference Marker 1300 is defined in this embodiment as the position where the sensor was initially registered this is an artificial Patient Reference Marker and used as such in FIG. 15. What is meant by this is since the movement sensor 1300 is attached to the Patient Reference Marker 1100 when this Patient Reference Marker 1100 is moved the output of the movement sensor 1300 actually indicates the relative movement of the Patient Reference Marker 1100 from an artificial Patient Reference Marker located at the position of the movement sensor 1300 when the Patient Reference Markers were last registered (i.e. when it began monitoring). It should be noted that a movement sensor may or may not output a value correlated with the magnitude or direction of the movement and may only provide an indication of whether movement has occurred or not. It is apparent that if the output matrix 3 shown in FIG. 14 were inputted into the flow chart in FIG. 9 the result would be a Case 2, in which the Patient Reference Marker 1110 and the Patient Reference Marker 1300 would be deemed accurate and Patient Reference Marker 1100 would be deemed inaccurate.

Although Patient Reference Marker 1300 is valid for analysis purposes since it is not an actual Patient Reference Marker per se (i.e. it is a pseudo Patient Reference Marker) it cannot be used for registration purposes (i.e. to register or re-register other objects). It is evident from the description of the scenario above that Patient Reference Markers when used to detect for accuracy errors and if found, determine the source of those errors, need not be physical Patient Reference Markers but may take the form of virtual or artificial Patient Reference Markers. Where an artificial Patient Reference Marker may have an arbitrarily defined position in the common coordinate space.

Although the flow charts in FIGS. 8 and 9 provide generic but effective processes for detecting for accuracy error and determining the source of that error in surgical navigation systems. There may be other exemplary processes that may be used that are truncated versions of these processes or specific to particular scenarios. For example if we consider the scenario in the right frame of FIG. 13. Where there are two Patient Reference Markers 1100 and 1110 and a movement sensor 1300. In this scenario Patient Reference Marker 1110 has shifted positions at an elapsed time after registration as indicated by arrow 1330. An alternate process that may be executed by the surgical navigation system to determine the accuracy error and the source of that error will be described as follows and is depicted as a flow chart in FIG. 15.

The flow chart begins by registering the two Patient Reference Markers 1100 and 1110 to the common coordinate space in order to be used for navigation during the surgery (step 1500). The next step 1505 is to acquire using the optical camera 1000 the relative position of Patient Reference Marker 1100 to the position Patient Reference Marker 1110 in the form of a vector. Next the system waits a predetermined time interval before continuing (step 1510). The system then acquires input from the movement sensor 1300 (step 1515) and determines if a movement of the Patient Reference Marker 1110 was detected (step 1520). If movement is detected than it can be probabilistically inferred that the Patient Reference Marker 1100 has moved and therefore must be re-registered (step 1525) to the common coordinate space in a process discussed below in further detail. Once this has occurred the system will loop back to step 1505 and start the process of detecting for accuracy error in the surgical navigation system and determining the source of that error again. If movement is not detected in step 1520 then the system progresses to the next step 1530. The system then re-acquires the relative position of the Patient Reference Marker 1100 to the position of the Patient Reference Marker 1110 in the form of a vector. The vector is then compared to the vector acquired at the time of the last registration. If the vectors have the same value the system will loop back to step 1505 and start the process of detecting for accuracy error in the surgical navigation system and determining the source of that error again. However if the values are different it can be probabilistically inferred that the Patient Reference Marker 1110 has moved and therefore must be re-registered (step 1525) to the common coordinate space in a process discussed below in further detail.

Although a minimum of two Patient Reference Markers and an additional reference marker are needed to determine the source of an accuracy error in a surgical navigation system, the use of a single Patient Reference Marker and an additional reference marker may be employed to simply detect an error. In the description of FIG. 5 above it is clear that this is accomplishable given the additional reference marker is a Patient Reference Marker. However there exists other combinations that may also be applicable to detect an accuracy error in a surgical navigation system. Such a combination would be to use a single sensor (shown as 1000 in FIG. 10) (such as the Polaris™ as manufactured by Northern Digital Incorporated) and a single Patient Reference Marker (shown as 1008). This combination would be able to detect an error using the same process depicted in FIG. 5 only that the sensor would also be a Patient Reference Marker. Another combination that would allow an accuracy error to be detected would be to use a single movement sensor (such as an accelerometer or gyroscope shown in FIG. 10 as 1012) in a combination with a single Patient Reference Marker (such as 1008 shown in FIG. 10). In this case an accuracy error may be detected by the navigation system if the movement sensor outputs a detected movement of the single Patient Reference Marker. It should be noted that a movement sensor would be any sensor that could be used to monitor the position of the Patient Reference Marker and detect if the Patient Reference Marker moved.

FIG. 16 also depicts an embodiment of a surgical navigation system with the same configuration as the scenario depicted in FIG. 7 section (b). In this embodiment the sensor S2 730 is an optical detector 1600 such as a camera, a stereo camera, a laser range finder, a 3D scanner, or etc. which specifically monitors one of the two Patient Reference Markers 1100 and 1110. The left frame of the figure depicts the surgical navigation system at the time of initial registration while the right frame depicts the surgical navigation system after the Patient Reference Marker 1110 has shifted positions. The sensor in this embodiment may be employed to detect for an accuracy error and if so determine the source of that error in the surgical navigation system in analogous ways to the movement sensor discussed above. In embodiments where this sensor 1600 is employed as a pseudo Patient Reference Marker its relative position from the Patient Reference Marker 1110 it's monitoring, will be defined as a physical position on the sensor (i.e. the camera will be the pseudo Patient Reference Marker position), unlike its bump sensor counterpart which has an artificial position.

FIG. 17 also depicts an embodiment of a surgical navigation system with the same configuration as the scenario depicted in FIG. 7 section (b). In this embodiment the sensor S2 730 is a surgical scope 1700. However in this embodiment unlike previous embodiments the sensor is also being registered by the sensor S1 (optical detector 1000 in the figure) to the common coordinate space, and an additional Patient Reference Marker 1710, in addition to the static Patient Reference Markers 1100 and 1110, being monitored is dynamic in that it does not have to necessarily remain in the same position throughout the surgical procedure to be deemed accurate. In this example a monocular camera 1700 is used to determine the position of a Patient Reference Marker 1710 through the use of computer vision and other methods as described by in the patent application CA/2014/050266, titled "SYSTEM AND METHOD FOR DYNAMIC VALIDATION, CORRECTION OF REGISTRATION FOR SURGICAL NAVIGATION" already incorporated in its entirety by reference for the purposes of any U.S. national phase application or Continuation-by-pass application claiming priority from this International PCT application. The Patient Reference Marker 1710 in this case is a medical instrument placed in view of the sensor 1700 which is locatable by both the sensor S2 730 (1700) and the sensor S1 740 (1000). The sensor 1700 in this embodiment may be employed to detect for an accuracy error and if so determine the source of that error in the surgical navigation system.

This surgical navigation system works by comparing the position of the reference marker 1710 as it is registered to the common coordinate space relative to the sensor, and any number (i.e. 1 to n) of other Patient Reference Markers. If the position of the reference marker 1710 when it is registered relative to the other Patient Reference Markers is not consistent to the position of the Patient Reference Marker 1710 when it is registered relative to the sensor 1700, then it can be probabilistically inferred that those Patient Reference Markers which yield inconsistent results are inaccurate and have shifted in position from the time of the last registration. For example in the embodiment depicted in FIG. 17 initially the reference marker 1710 position is registered relative to the Patient Reference Marker 1100 which is consistent with the reference marker position when it is registered relative to the sensor 1700. After the Patient Reference Marker 1100 shifts a distance $\beta$ (1720) the position of the reference marker 1710 also shifts position to location 1730 by the same distance $\beta$.

When the reference marker 1710 is registered relative to the sensors 1700 position it is assumed to be correctly positioned because the sensor relies on a different method to acquire the relative position of the reference marker 1710 then is used when acquiring its position relative to the Patient Reference Marker 1100. Therefore if the Patient Reference Marker 1710 is registered relative to a Patient Reference Marker other than the sensor 1700 and the resulting position registration is not equal to the position registration relative to the sensor, it can be probabilistically assumed that that Patient Reference Marker has shifted in position from the last registration of the surgical navigation system. It should be apparent from the description above that a Patient Reference Marker or reference marker may take the form of an object such a surgical instrument (mounted on reference marker 1710), that is periodically registered to the common coordinate space, where if the period is small enough the registration becomes equivalent to tracking.

Figure 18:
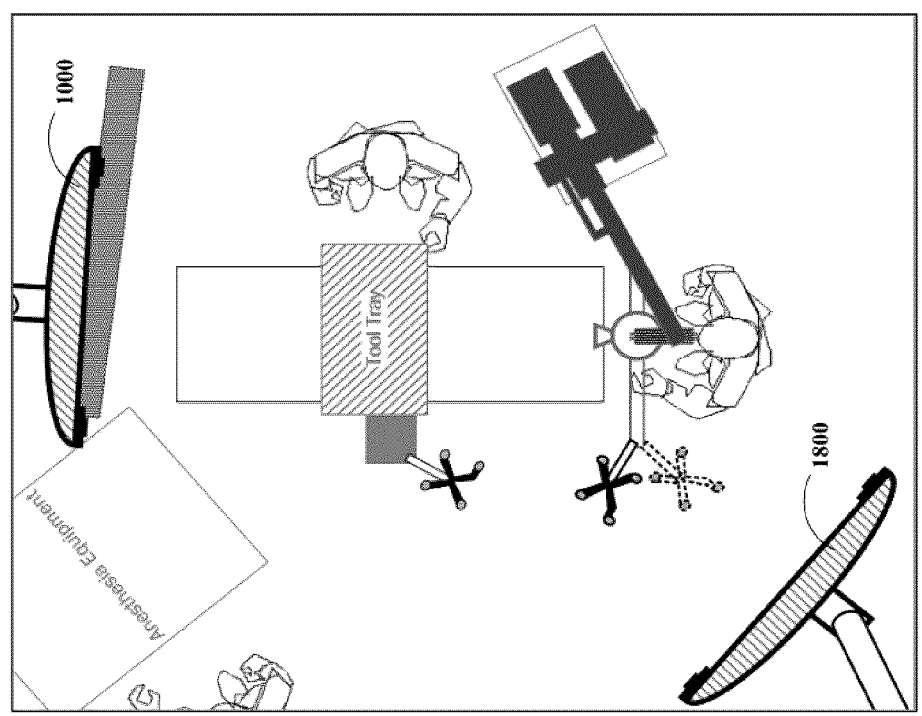
FIG. 18 illustrates an embodiment of a surgical navigation system employing a redundant stereo tracking camera.
Figure 19:
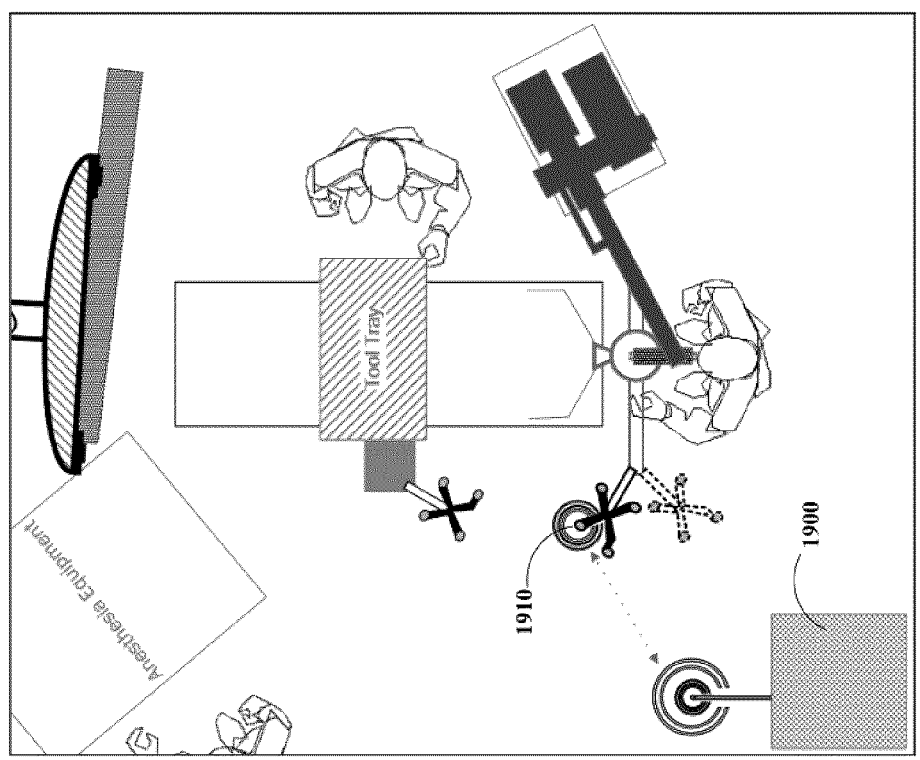
FIG. 19 illustrates an embodiment of a surgical navigation system employing a redundant tracking system.

FIGS. 18 and 19 both depict practical surgical navigation system embodiments with configurations consistent with scenario (c) in FIG. 7. In this scenario two sensors are employed for redundancy, one of the sensors, having a lower probability of shifting position is used as a "correct" reference (i.e. the reference that is taken to be accurate). In these embodiments a redundant tracking system such as a redundant optical system 1800 for registration shown in FIG. 18 or the redundant ultrasound or EM system 1900 for registration shown in FIG. 19 are used in combination with an optical system 1000. When utilizing the ultrasound or EM system however the Patient Reference Markers must be equipped with the correct hardware to be located by whatever redundant registration system may be employed. Such as an US or EM transmitter 1910.

If a Case 3 as described above were to occur then a redundant system for registration would be able to confirm whether a group of Patient Reference Markers were accurate or not. As acquired by the redundant system (S2 in scenario (c) of FIG. 7) (assumed to acquire the positions of the Patient Reference Markers or reference marker accurately), at the time of analysis to their positions relative to the redundant system at the time of the last registration. If any of the Patient Reference Markers are found to have changed position the group containing that Patient Reference Marker may be assumed to be inaccurate. The redundant system in this case being assumed to be accurately able to determine movement of the Patient Reference Markers.

The final scenario (d) in FIG. 7 depicts an embodiment in which the sensors used in scenario (b) in FIG. 7 as described above are used to monitor every Patient Reference Marker individually. It is apparent than in this scenario that any detected movement by any of the sensors S4-S7 would instantly reveal an inaccuracy error in the surgical navigation system. A practical example of this embodiment would be to employ movement sensors as described above on every Patient Reference Marker employed by the surgical navigation system. In this way any time a Patient Reference Marker shifted its position the surgical navigation system would be informed immediately and could correct for it using the re-registration process described below. It should be apparent from the description above that it needn't be detected that an accuracy error is present in the surgical navigation system prior to analysis of the system to determine the source of the accuracy error. In an embodiment the execution of a process to perform an accuracy error analysis of the surgical navigation system may be determining if an accuracy error has occurred while simultaneously determining the source of that inaccuracy. Such as is apparent from the previously given example where all Patient Reference Markers have attached motion sensors.

Re-Registration of an Inaccurate Reference Marker

In particular scenarios it may be desirable to re-register an inaccurate Patient Reference Marker. This is a relatively simple task to complete if there exists an additional Patient Reference Marker employed by the system that remains accurate (i.e. it hasn't shifted its position relative to the last time it was registered to the common coordinate space). Two exemplary situations in which this scenario could potentially occur would be Cases 2 and 3 as described above. Referring to FIG. 6 the left frame shows a surgical navigation system at the time of registration of the Patient Reference Markers to the common coordinate space. In this scenario the position of object 610 is accurately registered relative to two accurately registered Patient Reference Markers 620 and 600. The right frame of this figure depicts the same surgical navigation system only the Patient Reference Marker 600 has shifted position to 640 at an elapsed time after the last registration of the Patient Reference Markers. This leads to the inaccurate registration of the object in the common coordinate space shown at 670. The actual object 610 is registered to the common coordinate space 630 at the average of its position as determined relative to the two Patient Reference Markers 620 (shown at 610) and 640 (shown at 650). This results in the object being registered at 670. The inaccurate registration, at position 670 as opposed to position 610, results from the surgical navigation system using the coordinates of the object 610 ($rx_{\alpha n}$, $ry_{\alpha n}$) relative to the previously registered Patient Reference Markers 600 position ($x_\alpha, y_\alpha$) to calculate the objects registration position, as opposed to using the coordinates of the object 600 ($rx'_{\alpha n}$, $ry'_{\alpha n}$) relative to the new Patient Reference Markers 600 position ($x'_\alpha, y'_\alpha$) to calculate its registration point.

After determining which Patient Reference Markers are accurately positioned and inaccurately positioned the system can re-register the inaccurate Patient Reference Marker such that it becomes accurately registered at its new position. In the scenario depicted in the right frame of FIG. 6 this can be done by setting the position of the inaccurately registered Patient Reference Marker 600 at its actual position 640. As its actual position is acquired relative to the accurately positioned Patient Reference Marker 620. This would mean its coordinates would be set to the coordinate sum of the position of the accurately registered Patient Reference Marker 620 in the common coordinate space and the vector from the accurately registered Patient Reference Marker (620 in this scenario) to the inaccurately registered Patient Reference Marker (640 in this scenario) as acquired by a sensor, this process is shown as follows:

$$\vec{V}_{640\ 620} = (rx_{\beta n}, ry_{\beta n}) + (rx'_{\alpha n}, ry'_{\alpha n})$$

Resulting in the following equality for the re-registered Patient Reference Marker in the common coordinate space $$(x_\alpha, y_\alpha) = (x_\beta, y_\beta) + \vec{V}_{640\ 620} = (x_\beta, y_\beta) + [(rx_{\beta n}, ry_{\beta n}) + (rx'_{\alpha n}, ry'_{\alpha n})]$$

Where ($x_\alpha$, $y_\alpha$) is the new position of the Patient Reference Marker 600 as it is registered to the common coordinate space. The new registered position of the Patient Reference Marker 600 would now be accurately registered. However one additional step must be taken to assure no additional accuracy errors are caused by this Patient Reference Marker. This step is to re-register the object (or landmark(s)) to this new position of the Patient Reference Marker 640. This may be accomplished by calculating the vector from the new position of the Patient Reference Marker to the position of the object calculated relative to only the accurate Position Reference Marker (or Markers depending on the particular embodiment of the surgical navigation system). In the exemplary scenario provided in the right side of FIG. 6 this may be executed as follows $$(rx_{\alpha n}, ry_{\alpha n}) = [(x_\beta, y_\beta) + (rx_{\beta n}, ry_{\beta n})] - (x_\alpha, y_\alpha) = (rx'_{\alpha n}, ry'_{\alpha n})$$

where ($rx_{\alpha n}$, $ry_{\alpha n}$) is the position of the object 610 relative to the correctly registered Patient Reference Marker 640. It should be noted that a Patient Reference Marker need not be limited to Registering to just one accurate Patient Reference Marker. Its position can be re-registered as a calculated average of multiple accurately registered Patient Reference Markers. This can be accomplished in an analogous method to the method used to calculate the position of an object relative to two Patient Reference Markers as described above and shown in step 570 of FIG. 5.

Figure 20:
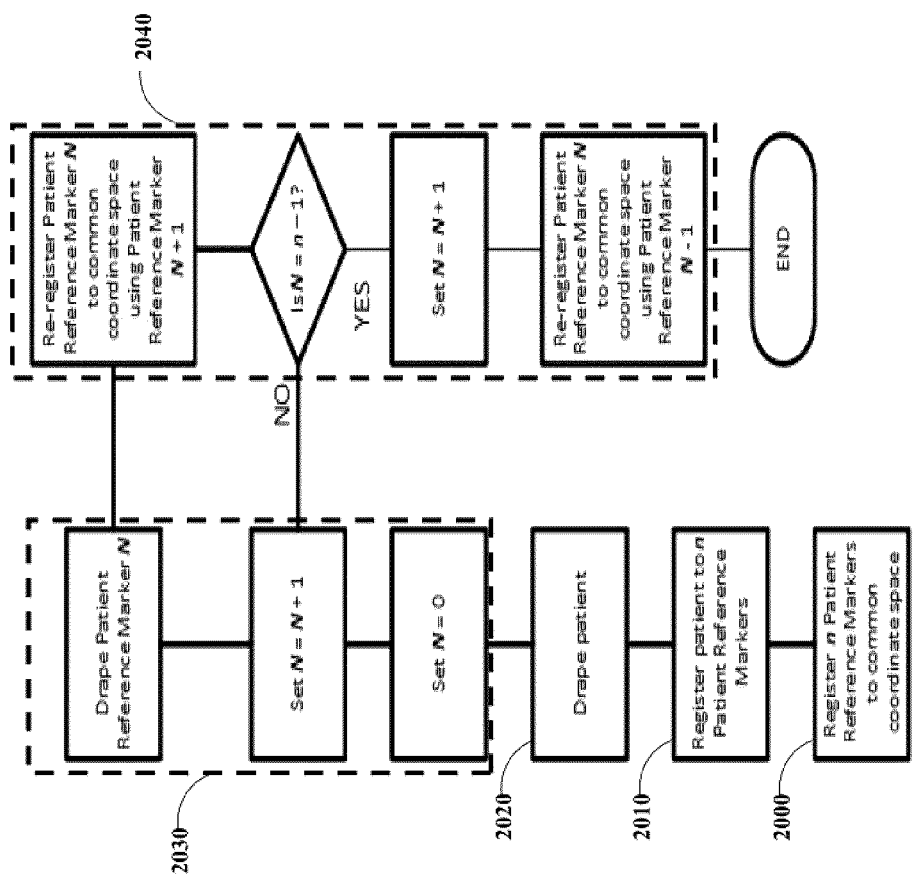
FIG. 20 illustrates a flow chart describing a process of registration at the initial registration step of a navigated surgical procedure

In an additional embodiment where this process of re-registering a Patient Reference Marker during a surgical procedure has utility is during an initial registration during which time the Patient Reference Markers are commonly draped. A high source of inaccuracy caused be Patient Reference Marker movement occurs during this step, as slight weight and forces from the draping procedure cause the Patient Reference Marker to move as is outlined by the paper [The Silent Loss of Navigation Accuracy; Research-Human-Clinical Studies; Vol. 72, No. 5, May 2013, pages 796-807]. To alleviate this cause of accuracy error in surgical navigation systems a general procedure for initial registration is provided in FIG. 20. In the flow chart it is suggested that two or more Patient Reference Markers initially be employed and registered in the common coordinate space 2000 followed by registering of the patient as well 2010. Once the patient is registered they can be draped 2020 along with one of the two or more Patient Reference Markers 2030. Subsequently the draped Patient Reference Marker(s) can then be re-registered to the non-draped Patient Reference Marker 2040. Once the re-registration is completed the next non-draped Patient Reference Marker can be draped and re-registered relative to the initially draped Patient Reference Marker. This process can be repeated multiple times for as many Patient Reference Markers are employed by the surgical navigation system being used.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

While the Applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims.

Therefore what is claimed is:

1. A method of determining a registration error source in a surgical navigation system, by way of a detection and adjustment system, comprising:
providing the detection and adjustment system, providing the detection and adjustment system comprising: providing a first plurality of sensors as a plurality of patient reference markers registered in a common coordinate space; providing a second plurality of sensors as a plurality of reference markers disposed in known positions relative to the plurality of patient reference markers, providing the first plurality of sensors comprising configuring the first plurality of sensors to individually monitor a position of each patient reference marker of the plurality of patient reference markers relative to another patient reference marker of the plurality of patient reference markers in the common coordinate space, providing the second plurality of sensors comprising configuring the second plurality of sensors to individually monitor a position of each reference marker of the plurality of reference markers relative to each patient reference marker of the plurality of patient reference markers, and providing the second plurality of sensors comprising providing at least one sensor thereof as one of a 3D scanner, a gyroscope, an accelerometer;
providing a computer processor configured by a set of executable instructions, storable in relation to a non-transient memory device, to:
receive a first output from the at least one sensor of the first plurality of sensors and determine, based on the first output, movement of each patient reference marker of the plurality of patient reference markers relative to another patient reference marker of the plurality of patient reference markers; and
receive a second output from the at least one sensor of the second plurality of sensors and determine, based on the second output, movement of each reference marker of the plurality of reference markers relative to each patient reference marker of the plurality of patient reference markers;
registering the plurality of patient reference markers in a common coordinate space by operating the computer processor;
positioning the plurality of reference markers in known positions relative to the plurality of patient reference markers by operating the computer processor;
registering a patient in an operating space containing the registered plurality of patient reference markers by operating the computer processor;
draping a first patient reference marker of the plurality of patient reference markers, thereby leaving a second patient reference marker of the plurality of patient reference markers undraped;
re-registering the first patient reference marker to the second patient reference marker by operating the computer processor;
draping the second patient reference marker;
re-registering the second patient reference marker to the first patient reference marker by operating the computer processor;
individually monitoring a position of each patient reference marker of the plurality of patient reference markers relative to another patient reference marker of the plurality of patient reference markers in the common coordinate space and a position of each reference marker relative to the first patient reference marker by operating the computer processor;
upon detecting a change in position of each patient reference marker of the plurality of patient reference markers relative to another patient reference marker of the plurality of patient reference markers, determining whether each reference marker of the plurality of reference markers has changed position relative to the first patient reference marker of the plurality of patient reference markers by operating the computer processor; and
by operating the computer processor, performing one of:
if the change in the position of the first patient reference marker of the plurality of patient reference markers relative to another patient reference marker of the plurality of patient reference markers is detected, designating movement of the first patient reference marker; and
if the change in the position of the first patient reference marker of the plurality of patient reference markers relative to another patient reference marker of the plurality of patient reference markers is not detected, designating movement of a second patient reference marker of the plurality of patient reference markers, thereby instantly revealing an inaccuracy error while simultaneously determining a source thereof.

2. The method according to claim 1, wherein positioning the plurality of reference markers comprises providing at least one reference marker of the plurality of reference markers as at least one patient reference marker registered to the common coordinate space.

3. The method according to claim 1,
wherein providing the second plurality of sensors as the plurality of reference marker markers comprises positioning the plurality of reference markers in known positions relative to all patient reference markers of the plurality of patient reference markers, and
wherein determining comprises:
determining whether a position of each at least one reference marker has changed relative to each patient reference marker; and
by operating the computer processor, performing one of:
designating movement of each patient reference marker for which the position of such each patient reference marker has changed; and
designating non-movement of each reference marker for which the position of such each patient reference marker has not changed.

4. The method according to claim 1, wherein providing the second plurality of sensors as comprises providing at least one sensor of the second plurality of sensors as one of an electromagnetic tracking system, an ultrasound tracking system, an optical tracking system, an optical camera, an infrared camera, a stereo camera, and a laser range finder.

5. The method according to claim 4, wherein providing the at least one sensor of the second plurality of sensors comprises providing the optical camera as an optical tracking camera.

6. The method according to claim 1, wherein positioning the plurality of reference markers comprises providing at least one reference marker of the plurality of reference markers as an object registered to the common coordinate space.

7. A detection and adjustment system for determining a registration error source in a surgical navigation system, comprising
a first plurality of sensors comprising a plurality of patient reference markers registered in a common coordinate space, the first plurality of sensors configured to individually monitor a position of each patient reference marker of the plurality of patient reference markers relative to another patient reference marker of the plurality of patient reference markers in the common coordinate space;
a second plurality of sensors comprising a plurality of reference markers disposed in known positions relative to the plurality of patient reference markers, the second plurality of sensors configured to individually monitor a position of each reference marker of the plurality of reference markers relative to each patient reference marker of the plurality of patient reference markers, and at least one sensor of the second plurality of sensors comprising one of a 3D scanner, a gyroscope, an accelerometer;
a computer processor configured by a set of executable instructions, storable in relation to a nontransient memory device, to:
receive a first output from the at least one sensor of the first plurality of sensors and determine, based on the first output, movement of each patient reference marker of the plurality of patient reference markers relative to another patient reference marker of the plurality of patient reference markers; and
receive a second output from the at least one sensor of the second plurality of sensors and determine, based on the second output, movement of each reference marker of the plurality of reference markers relative to each patient reference marker of the plurality of patient reference markers;
registering the plurality of patient reference markers in a common coordinate space by operating the computer processor;
positioning the plurality of reference markers in known positions relative to the plurality of patient reference markers by operating the computer processor;
registering a patient in an operating space containing the registered plurality of patient reference markers by operating the computer processor;
draping a first patient reference marker of the plurality of patient reference markers, thereby leaving a second patient reference marker of the plurality of patient reference markers undraped;
re-registering the first patient reference marker to the second patient reference marker by operating the computer processor;
draping the second patient reference marker;
re-registering the second patient reference marker to the first patient reference marker by operating the computer processor;
individually monitoring a position of each patient reference marker of the plurality of patient reference markers relative to another patient reference marker of the plurality of patient reference markers in the common coordinate space and a position of each reference marker relative to the first patient reference marker by operating the computer processor;
upon detecting a change in position of each patient reference marker of the plurality of patient reference markers relative to another patient reference marker of the plurality of patient reference markers, determining whether each reference marker of the plurality of reference markers has changed position relative to the first patient reference marker of the plurality of patient reference markers by operating the computer processor; and
by operating the computer processor, performing one of:
if the change in the position of the first patient reference marker of the plurality of patient reference markers relative to another patient reference marker of the plurality of patient reference markers is detected, designating movement of the first patient reference marker; and
if the change in the position of the first patient reference marker of the plurality of patient reference markers relative to another patient reference marker of the plurality of patient reference markers is not detected, designating movement of a second patient reference marker of the plurality of patient reference markers,
thereby instantly revealing an inaccuracy error while simultaneously determining a source thereof.

8. The system according to claim 7, wherein at least one reference marker of the plurality of reference markers comprises a patient reference marker registered to the common coordinate space.

9. The system according to claim 7, wherein at least one sensor of the second plurality of sensors is also registered to the common coordinate space.

10. The system according to claim 7,
wherein the at least one reference marker of the plurality of reference markers is operable as at least one patent reference marker of the plurality of patient reference markers, and
wherein the at least one sensor of the second plurality of sensors is operable as at least one pseudo patient reference marker,
whereby analysis is improvable for determining existence of any accuracy error exists and the source of any such accuracy error.

11. The system according to claim 10, wherein at least one sensor of the second plurality of sensors further comprises one of: an electromagnetic tracking system, an ultrasound tracking system, an optical tracking system, an optical camera, an infrared camera, a stereo camera, and a laser range finder.

12. The system according to claim 11, wherein the optical camera comprises an optical tracking camera.

13. The system according to claim 7, wherein the at least one reference marker of the plurality of reference markers comprises an object registered to the common coordinate space.

14. The system according to claim 7, wherein positioning comprises providing the at least one reference marker of the plurality of reference markers as a patient reference marker registered to the common coordinate space.

15. The system according to claim 7, wherein positioning comprises providing at least one sensor as the at least one reference marker of the plurality of reference markers.

16. The system according to claim 15,
wherein providing the at least one sensor as the at least one reference marker comprises positioning the at least one reference marker in a known position relative to all patient reference markers of the plurality of patient reference markers, and
wherein determining comprises:
determining whether a position of each at least one reference marker has changed relative to each patient reference marker of the plurality of patient reference markers; and
by operating the computer processor, performing one of:
designating movement of each at least one reference marker for which the position of such each at least one reference marker has changed; and
designating non-movement of each reference marker for which the position of such each at least one reference marker has not changed.

17. The system according to claim 15, wherein providing the at least one sensor as a reference marker further comprises providing at least one of: an electromagnetic tracking system, an ultrasound tracking system, an optical tracking system, an optical camera, an infrared camera, a stereo camera, and a laser range finder.

18. The system according to claim 15, wherein monitoring comprises using an optical tracking camera.

* * * * *